(12) United States Patent
Paspa et al.

(10) Patent No.: US 9,788,952 B2
(45) Date of Patent: Oct. 17, 2017

(54) BURR HOLE COVERS AND METHODS FOR USING SAME

(71) Applicant: NeuroPace, Inc., Mountain View, CA (US)

(72) Inventors: Paul Paspa, Los Gatos, CA (US); Greg Sandoval, San Jose, CA (US); Alfonso Chavez, San Jose, CA (US); Dennis Potts, Scotts Valley, CA (US); John Dunagan Pearson, Mountain View, CA (US)

(73) Assignee: NeuroPace, Inc., Mountain View, CA (US)

( * ) Notice: Subject to any disclaimer, the term of this patent is extended or adjusted under 35 U.S.C. 154(b) by 271 days.

(21) Appl. No.: 13/792,119

(22) Filed: Mar. 10, 2013

(65) Prior Publication Data
US 2013/0304216 A1   Nov. 14, 2013

Related U.S. Application Data

(60) Provisional application No. 61/645,593, filed on May 10, 2012.

(51) Int. Cl.
| A61F 2/02 | (2006.01) |
| A61F 2/28 | (2006.01) |
| A61N 1/05 | (2006.01) |

(52) U.S. Cl.
CPC .......... *A61F 2/2875* (2013.01); *A61N 1/0539* (2013.01)

(58) Field of Classification Search
CPC ................ A61N 1/0539; A61N 1/0534; A61B 2019/208; A61B 19/201; A61B 5/6864; A61M 2039/025; A61M 2210/0687

USPC ........................................................ 623/17.19
See application file for complete search history.

(56) References Cited

U.S. PATENT DOCUMENTS

| 4,328,813 | A |   | 5/1982 | Ray |
| 5,464,446 | A |   | 11/1995 | Dreessen |
| 5,843,150 | A |   | 12/1998 | Dreessen et al. |
| 5,865,842 | A |   | 2/1999 | Knuth et al. |
| 5,865,843 | A |   | 2/1999 | Baudino et al. |
| 5,927,277 | A | * | 7/1999 | Baudino et al. ............. 600/386 |

(Continued)

FOREIGN PATENT DOCUMENTS

| WO | 0176498 | 10/2001 |
| WO | 2004103468 | 12/2004 |

*Primary Examiner* — David Isabella
*Assistant Examiner* — Christine Nelson
(74) *Attorney, Agent, or Firm* — Loza & Loza, LLP; David S. Sarisky

(57) ABSTRACT

A burr hole cover includes a cap or cap assembly and a retainer and is configured to be partially positioned within a burr hole formed in a patient. The retainer has a cap-receiving aperture; a plurality of grooves provided in the retainer and a plurality of cut-outs wherein each cut-out is provided at an end of each groove towards the outer perimeter of the retainer. A channel may be provided at an opposite end of each groove vertically-extending from the top to the bottom of the retainer to encourage a medical device segment to remain in a groove during installation of the burr hole cover. The burr hole cover may be used to secure segments of medical devices relative to a burr hole and to allow a range of lateral motion for the portion(s) of the medical device(s) extending proximally out of the corresponding groove.

12 Claims, 14 Drawing Sheets

(56) References Cited

U.S. PATENT DOCUMENTS

| | | |
|---|---|---|
| 6,044,304 A | 3/2000 | Baudino |
| 6,134,477 A | 10/2000 | Knuteson et al. |
| 6,210,417 B1 | 4/2001 | Baudino et al. |
| 6,319,241 B1 | 11/2001 | King et al. |
| 6,321,104 B1 | 11/2001 | Gielen et al. |
| 6,795,737 B2 | 9/2004 | King et al. |
| 6,810,285 B2 | 10/2004 | Pless et al. |
| 6,902,569 B2 | 6/2005 | Parmer et al. |
| 7,204,840 B2 | 4/2007 | Skakoon et al. |
| 7,235,084 B2 | 6/2007 | Skakoon et al. |
| 7,580,756 B2 | 8/2009 | Schulte et al. |
| 7,604,644 B2 | 10/2009 | Schulte et al. |
| 7,636,596 B2 | 12/2009 | Solar |
| 7,637,915 B2 | 12/2009 | Parmer et al. |
| 7,660,621 B2 | 2/2010 | Skakoon et al. |
| 7,704,260 B2 | 4/2010 | Skakoon et al. |
| 7,744,606 B2 | 6/2010 | Miller et al. |
| 7,766,394 B2 | 8/2010 | Sage et al. |
| 7,766,922 B1 | 8/2010 | Daglow et al. |
| 7,815,651 B2 | 10/2010 | Skakoon et al. |
| 7,828,809 B2 | 11/2010 | Skakoon et al. |
| 7,833,231 B2 | 11/2010 | Skakoon et al. |
| 7,857,820 B2 | 12/2010 | Skakoon et al. |
| 7,949,410 B2 | 5/2011 | Rodriguez |
| 7,976,530 B2 | 7/2011 | Johnson et al. |
| 7,988,674 B2 | 8/2011 | Adams et al. |
| 8,116,850 B2 | 2/2012 | Solar |
| 8,152,792 B1 * | 4/2012 | Kornel .......... 604/540 |
| 8,192,445 B2 | 6/2012 | Parmer et al. |
| 8,845,656 B2 | 9/2014 | Skakoon et al. |
| 8,911,452 B2 | 12/2014 | Skakoon et al. |
| 2005/0182421 A1 | 8/2005 | Schulte et al. |
| 2005/0182422 A1 | 8/2005 | Schulte |
| 2005/0182424 A1 | 8/2005 | Schulte et al. |
| 2005/0182425 A1 | 8/2005 | Schulte et al. |
| 2009/0112327 A1 | 4/2009 | Lane et al. |
| 2009/0306750 A1 | 12/2009 | Boling et al. |
| 2009/0326610 A1 | 12/2009 | Pless et al. |
| 2010/0179563 A1 | 7/2010 | Skakoon et al. |
| 2010/0312193 A1 * | 12/2010 | Stratton ........ A61M 39/02 604/175 |
| 2011/0270187 A1 | 11/2011 | Nelson |
| 2013/0066410 A1 | 3/2013 | Funderburk |

* cited by examiner

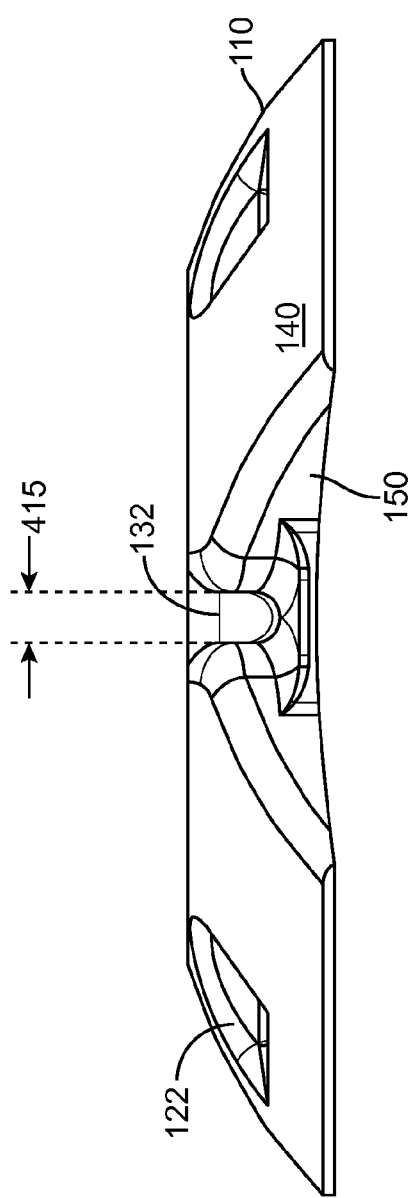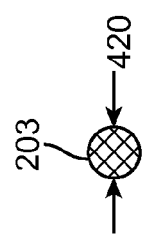
FIG. 4A
FIG. 4B

BURR HOLE COVERS AND METHODS FOR USING SAME

CROSS-REFERENCE TO RELATED APPLICATIONS

This application claims priority to and benefit of U.S. Provisional Patent Application No. 61/645,593 filed May 10, 2012, entitled "Burr Hole Covers and Methods for Using Same" by Paul Paspa, et al., and assigned to the assignee of the present application. Provisional Application No. 61/645,593 is hereby incorporated herein, in its entirety, by reference.

FIELD OF THE INVENTION

The present technology relates generally to apparatuses and methods for securing a medical instrument, such as a lead, within a burr hole.

BACKGROUND

Increasingly, leads associated with electrodes or other components that can be used for sensing signals from or delivering a form of modulation to a patient's neural tissue are partially implanted in a patient's brain through a burr hole that is formed (e.g., using a drill fitted with a special drill bit) in the patient's cranium (cranial bone or skull). To prepare for forming the burr hole, the scalp over the site is removed or temporarily retracted. After the burr hole is formed, a portion of a lead is implanted through the burr hole so that electrodes or other components that are associated with the lead are distally located at a desired target or targets in the brain. Once a distal portion of a lead is positioned at the target(s), it may be desirable to secure a proximal portion of the lead in the vicinity of the burr hole in the hopes of minimizing the extent to which the distal portion of the lead will shift, for example, away from the target(s), for so long as the lead is intended to remain implanted in the patient and to function for its intended purpose(s).

BRIEF DESCRIPTION OF THE DRAWINGS

FIG. 4A is a side elevational view of a retainer of a burr hole cover according to an embodiment.

FIG. 4B is an end view of a generally cylindrical lead that may comprise a medical device with which embodiments of the burr hole cover may be used.

Figure 1:
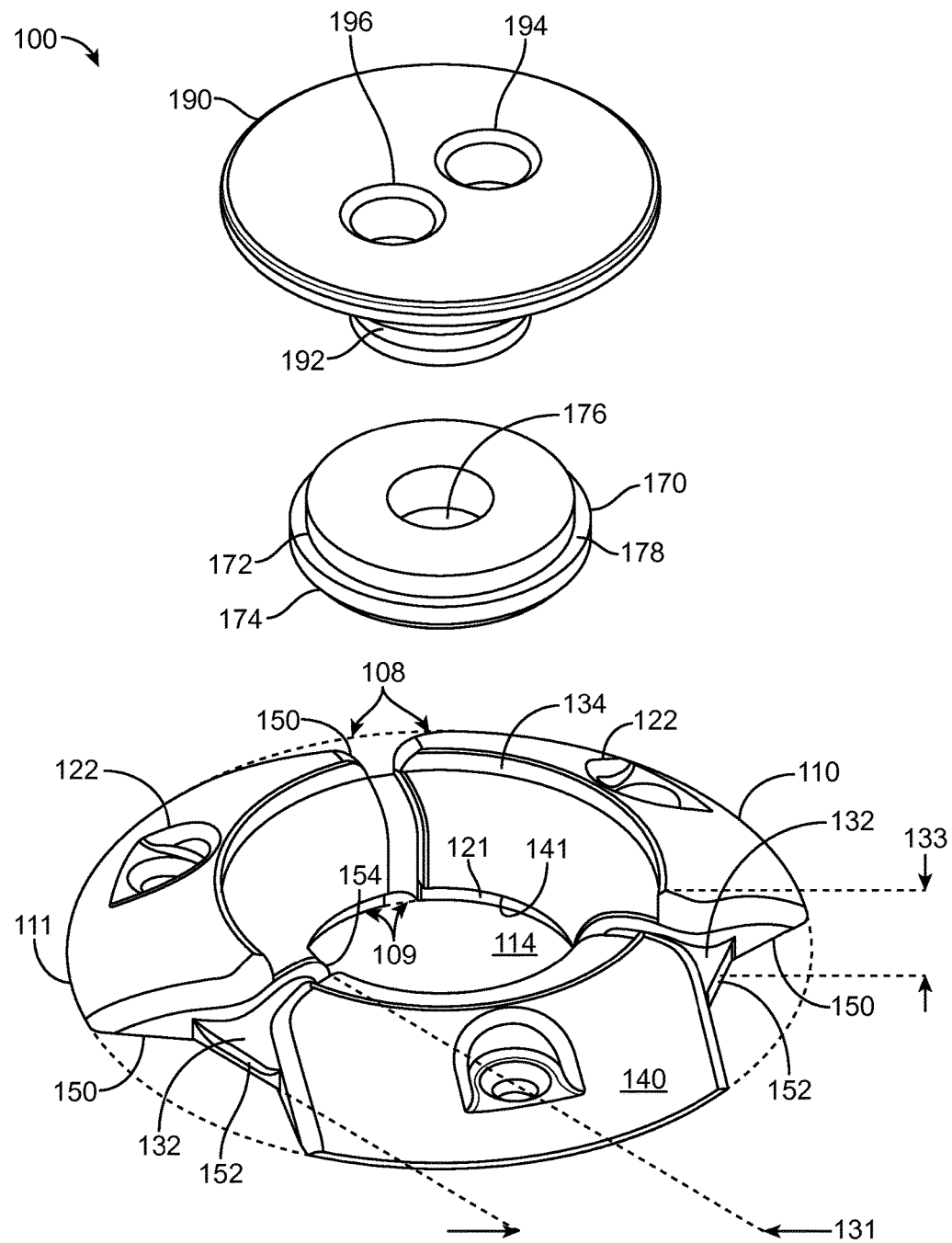
FIG. 1 is an exploded perspective view of a burr hole cover according to an embodiment.

The drawings referred to in this description should not be understood as being drawn to scale unless specifically noted.

DESCRIPTION OF EMBODIMENTS

Various embodiments are described below, with reference to detailed illustrative embodiments, in the context of burr hole covers. It will be apparent that the apparatuses and methods described herein can be embodied in a wide variety of forms. Consequently, the specific structural and functional details disclosed herein are representative and do not limit the scope of embodiments.

Embodiments of a burr hole cover are provided for securing a segment of a medical device relative to a burr hole formed in the cranium of a patient when a distal portion of the medical device is implanted or otherwise introduced into the burr hole interiorly of the patient. The embodiments are described primarily with reference to the medical device being an electrode-bearing lead, such as might be used in an application for deep brain stimulation or direct brain stimulation such as responsive stimulation such as those applications under investigation by NeuroPace, Inc. of Mountain View, Calif. It should be appreciated, however, that the burr hole cover may be used with good results to secure a segment of a different type of medical device, such as a catheter with an appropriate diameter or other medical instrument, relative to a burr hole prior to and/or during use of the medical device in its intended application. Similarly, it should be appreciated that, in some circumstances, embodiments of a burr hole cover described herein may be used to secure more than one medical device simultaneously (e.g., two leads) for some applications.

Generally, when a medical device is introduced to a target position interiorly of a patient's cranium, it is desirable for the distal portion of the medical device not to move appreciably from that target. More particularly, in the case where the medical device is a deep brain lead with one or more electrodes associated with a distal portion thereof, it is desirable to minimize the degree to which the distal portion moves once it has been positioned at the target. For example, in an application in which one or more of the electrodes are intended to be used in stimulation pathways to deliver a form of electrical stimulation therapy to the tissue surrounding or adjacent the electrodes, and the electrodes on the distal portion of the lead are positioned at a desired target area of the patient's brain (for example, the subthalamic nucleus (STN) or a brain location suspected or known to be a focus or related to a focus of an epileptic seizure), it would be desirable to avoid moving the electrodes from that target area during the time over which it is anticipated the therapy may be delivered. Similarly, in an application in which electrodes or other elements associated with the distal portion of a lead are going to be used to sense physiological activity from a location in the brain, it would be desirable to avoid dislodging the sensors from the desired sensing location once the lead is implanted for so long as sensing potentially may occur.

Applications are known or under investigation in which leads for delivering stimulation therapy (and/or sensing and/or recording the electrical activity of nerve cells) are implanted and then left in place for extended period of time (e.g., on the order of years provided the leads remain intact and uncompromised and otherwise without complications). Desirably, then, the means and methods by which the lead is discouraged from moving away from the target area will be relatively robust and durable and therefore well-suited for chronic or long-lasting applications involving the lead or other medical device. It may be desirable to form a burr hole cover from a material or materials that will not interfere with any imaging procedure to which the patient might be subjected (e.g., materials that will not distort or obstruct an image) and/or from material(s) (e.g., non-magnetic materials) that will not contraindicate an imaging procedure in the first instance. In addition, the material(s) from which the burr hole cover is formed desirably will not degrade appreciably over time and will be biocompatible with any body surfaces (e.g., cranial bone) and body fluids (e.g., cerebral spinal fluid) with which the burr hole cover may come in contact throughout the time the burr hole cover is installed in the patient.

Referring to FIGS. 1-18, embodiments of burr hole covers and embodiments of methods of using burr hole covers will be described.

FIG. 1 is an exploded view of an embodiment of a three-component burr hole cover 100. The three components are a retainer 110, a gasket 170, and a cap 190. Herein, when the gasket is assembled with the cap, the combination will be referred to as the gasket-and-cap assembly. In some embodiments, the gasket 170 will be provided to users preassembled with the cap 190 in a gasket-and-cap assembly 880 (see FIGS. 8-9). Each component of the burr hole cover 100 is described in more detail below.

Figure 2A:
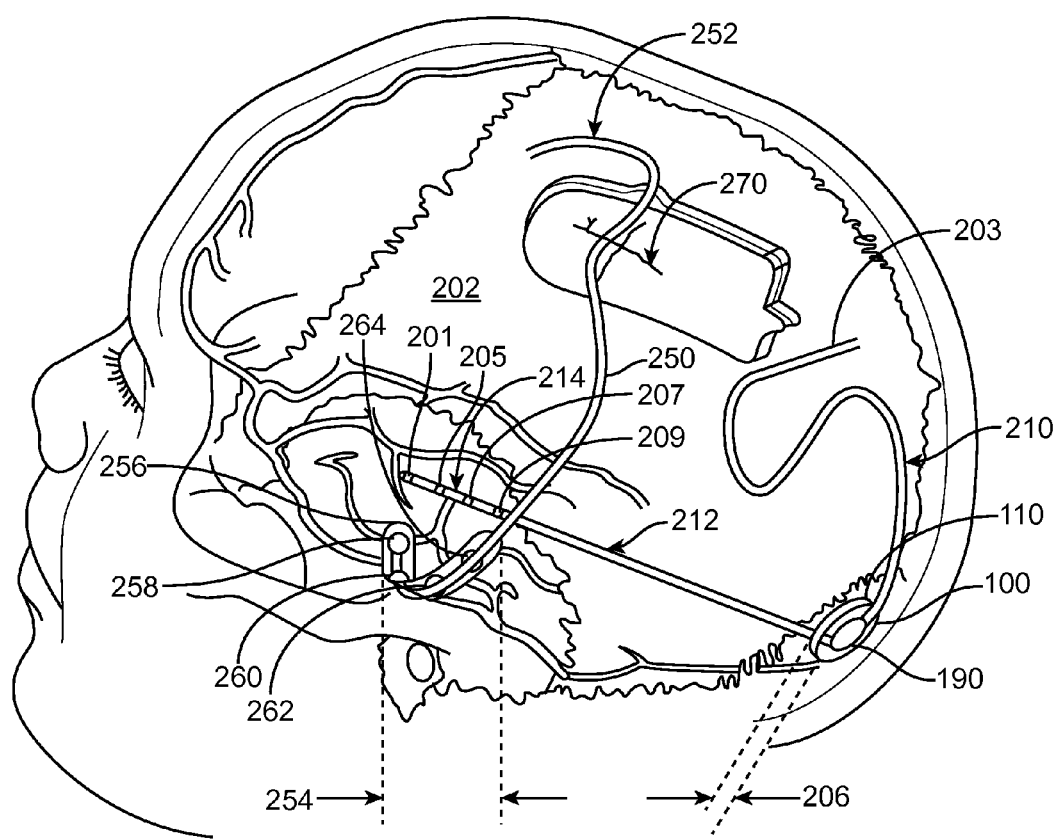
FIG. 2A is a schematic view of a patient's skull with electrode-bearing brain leads, at least one of which has a distal portion thereof implanted in the patient and a proximal portion thereof secured at a burr hole by a burr hole cover.
Figure 2B:
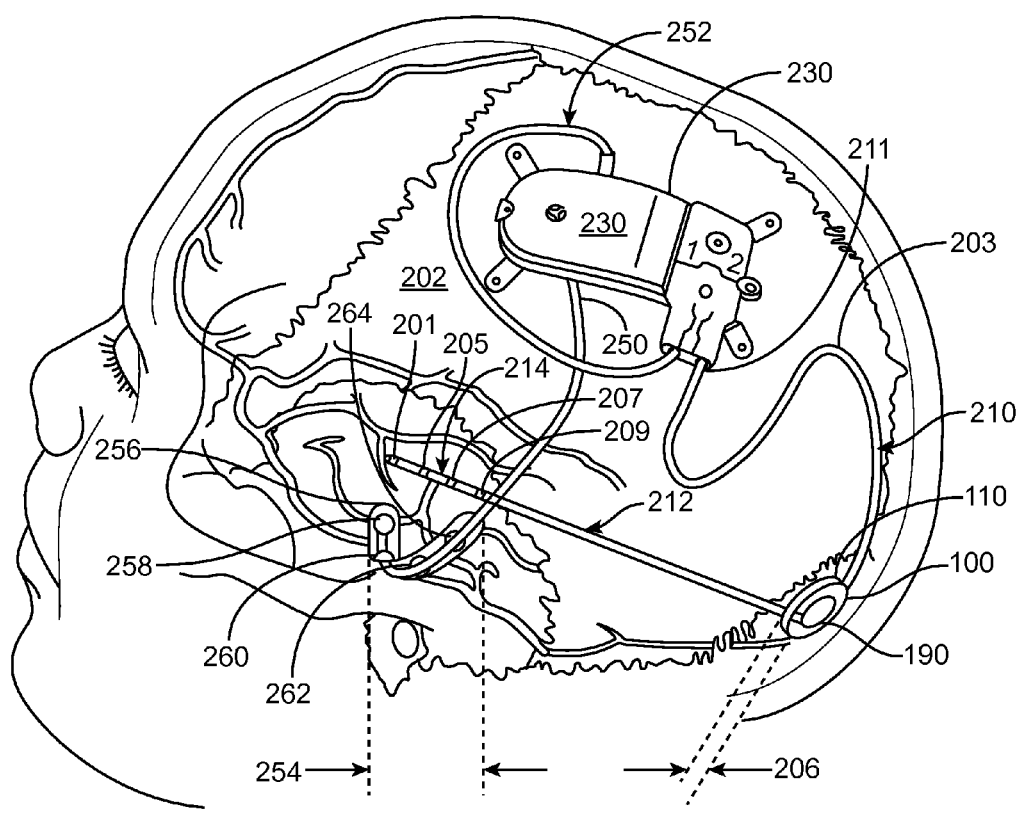
FIG. 2B is the schematic view of FIG. 2A, after an implantable neurostimulator has been implanted in the patient and the electrode-bearing brain leads have been connected to the neurostimulator.

Referring now to FIGS. 2A-2B, a burr hole cover 100 is used to secure a segment 206 of a proximal portion 210 of a deep brain lead 203 in a burr hole formed in a cranium 202 of a patient. A distal portion 212 of the deep brain lead 203 is shown implanted in the brain tissue of the patient, and passing through a burr hole in which a burr hole cover 100 is installed. Exteriorly of the patient's skull, the proximal portion 210 of the deep brain lead 203 is shown arranged on top of the patient's skull.

An implanted neurostimulator 230 is also shown in FIG. 2B to which a proximal end 211 of the deep brain lead 203 is connected (e.g., for allowing stimulation to be delivered to or physiological activity of the brain to be sensed and/or recorded).

A second brain lead is also shown in FIGS. 2A-2B, namely, a cortical strip lead 250. The cortical strip lead 250 has a distal portion 254 that includes a distal strip 256 which contains four disk electrodes 258, 260, 262, and 264 that are intended to be implanted so that each rests against a surface or adjacent a surface of the brain. A proximal portion 252 of the cortical strip lead 250 is shown extending exteriorly of the cranial cavity through a stitched-together incision 270 in the patient's scalp in FIG. 2A, rather than through a burr hole or via a burr hole cover. It will be appreciated that a cortical strip lead does not have to be routed as shown in FIGS. 2A and 2B, rather a proximally-extending portion 252 of a cortical strip lead may be routed through a burr hole, and thus used with a burr hole cover according to embodiments, as is the case with the deep brain lead 203.

Referring again to the deep brain lead 203 shown in FIGS. 2A and 2B, four ring electrodes 201, 205, 207, and 209 are provided at a distal end 214 of the distal portion 212 of the deep brain lead 203. In a method according to an embodiment, a surgeon inserts the distal portion 212 of the brain lead 203 in the patient's brain so that the ring electrodes 201, 205, 207, and 209 on a distal end 214 of the distal portion 212 are in or are adjacent a desired structure or structures or other target in the brain tissue. The surgeon may locate the desired implant site for the electrodes using one or more means such as forms of imaging (e.g., MRI) or microelectrode recordings. The surgeon may manipulate the distal portion 212 of the deep brain lead 203 to the target location (s) using stereotactic equipment and methods or some other suitable technique or approach.

Once the distal end 214 and its associated electrodes 201, 205, 207, and 209 are located where the surgeon wants them to chronically remain, the surgeon or one assisting the surgeon grabs (either with fingers or using a surgical instrument or tool) the proximal portion 210 of the deep brain lead 203 that extends exteriorly of the burr hole. Then the surgeon positions the retainer 110 in the burr hole, secures the segment 206 of the proximal lead portion to be secured by the burr hole cover 100 in the burr hole cover, and then inserts the gasket-and-cap assembly 880 into the retainer 110 and pushes it down in the direction of the brain to affix the lead segment 206 relative to the burr hole cover 100. Depending on the features with which the retainer 110 is provided, before the distal portion 212 of the lead 203 is implanted in the patient, the retainer 110 may need to be threaded over the lead 203 so that the lead is passing through the cap-receiving aperture 114 (not shown in FIG. 2) of the retainer 110. Alternatively, the burr hole can be formed and the retainer 110 placed in, and, if applicable, secured to, the burr hole, and the lead 203 can be implanted through the cap-receiving aperture 114.

After the lead 203 is implanted and the burr hole cover 100 is partially or fully installed to secure the lead 203, and as is shown in FIG. 2B, a proximal end 211 of the proximal portion 210 of the lead 203 may be routed to and connected to another implanted device, such as the neurostimulator 230. Alternatively, a proximal end may be connected to a piece of external equipment (not shown in the figures) that can generate a form of neuromodulation to be communicated through the lead and/or monitor and/or record signals sensed from the patient's brain via the lead. When the lead 203 is intended to remain in place chronically, after the procedure to implant the lead is completed and the burr hole cover 100 is installed, the burr hole cover 100 may be re-covered with the retracted or removed section of scalp or with a prosthetic or synthetic scalp substitute.

Once all of the components 110, 170 and 190 of the burr hole cover 100 have been installed (which installation is described more fully below), the distal portion 212 of the lead will be discouraged from moving appreciably relative to the segment 206 of the proximal lead portion 210 that is situated in the burr hole cover 100, even when the proximal portion 210 that extends proximally away from the point of affixation at the burr hole cover 100 is manipulated (for example, when the surgeon attaches a proximal end to another device internally or externally of the patient or when the patient fiddles or fusses with the proximal portion 210 during the time when the lead remains chronically implanted in the patient.)

When the medical device being secured is an electrode-bearing brain lead such as the lead 203, one or more conductors may be provided in the lead to permit electrical connectivity between the electrodes on the distal end 214 and a lead proximal end (such as lead proximal end 211 shown in FIG. 2B) that ultimately is connected either to another implanted device, such as the neurostimulator 230, or to an external component not implanted in the patient. If there are multiple conductors in a lead 203, the conductors may be insulated from each other within the body of the lead 203. If the lead 203 (or other medical device) is to be introduced into brain tissue, the lead 203 may be formed from materials that render it more malleable or floppy than stiff, for example, to minimize the likelihood that the lead will interfere with the tissue in which (or against which) it is implanted or otherwise cause trauma at and around the implant site. In a case where a lead 203 is not inherently stiff, the lead 203 may be provided with a lumen or cavity that extends almost all of the way through or just partially through the body of the lead to accommodate a stiffener, such as a stylet, which can remain in place during the procedure to implant the lead and thereafter can be removed.

If the medical device to be secured with a burr hole cover includes conductors, then the risk of compromising the conductors (e.g., breaking or overstressing the conductors) either during or subsequent to installation of the burr hole cover desirably should be minimized. Similarly, if the medical device is a lead that is not inherently stiff but has its stiffness supplemented with a stiffener such as a stylet that is ultimately intended to be withdrawn and removed from the lead, then the burr hole cover will need to be adequate to affix the lead in the vicinity of the burr hole with the stylet absent from the lead body. In some cases, it may be desirable to affix the lead with the burr hole cover before withdrawing the stylet (for example, to minimize the likelihood that the distal portion of the lead will be dislodged from the intended target area during the affixation process). In other cases, it may be desirable to affix the lead with the burr hole cover after the stylet has been removed from the lead body (for example, to avoid the possibility that an installed or partially installed burr hole cover will interfere with withdrawing the stylet from the lead body or will result in unintended movement of the distal portion of the lead). Depending on the features with which the burr hole cover 100 is provided, any stylet may need to be withdrawn proximally from the lead past the segment 206 that is to be secured in the burr hole cover 100 before the segment can be secured.

In addition to the nature of the medical device (e.g., lead with conductors extending therethrough or some other type of medical instrument such as a catheter) and the relative stiffness of the medical device (e.g., whether it is stiff or has a removable stiffener), another criterion for selecting a burr hole cover is the degree of security desired at the segment 206 of the proximal lead portion 210 to be situated in the burr hole cover 100. For example, in some applications, it may be undesirable for the distal portion 212 of a lead 203 to move more than a fraction of an inch once the distal end 214 has been positioned at a target area. This might be the case where one or more electrodes (such as one or more of the electrodes 201, 205, 207, and 209) are intended to remain at or near a relatively small physical target in the brain (e.g., the STN). In other applications, it may be acceptable for the distal end 214 of the distal portion 212 to shift or migrate more over the period of time in which the lead 203 remains implanted in the patient (e.g., when electrodes are being used to stimulate or sense from a broader physical target area or to stimulate or sense at some point in a functional pathway (such as a known or suspected brain circuit), as contrasted to a physical structure). In some applications under investigation that use an implanted neurostimulator together with one or more implanted electrode-bearing leads to treat epilepsy, more potential movement of the distal end 214 of the lead 203 may be tolerable than in other applications, such as an application using deep brain stimulation to treat the symptoms of a movement disorder.

Referring now to FIGS. 1-11, embodiments of a burr hole cover 100 are characterized by a retainer 110 having a plurality of features that will be described for convenience with reference to surfaces or areas. More particularly, the retainer 110 has an undersurface 111 (see also the bottom view of the retainer 110 shown in FIG. 7) that is intended to at least partially contact or connect to the patient's cranium 202 when the burr hole cover 100 is installed and a top surface 140. The top surface 140 encompasses all surfaces of the retainer 110 other than the undersurface 111 and extends from a retainer outer perimeter 108 to a retainer inner perimeter 109. The top surface 140 may be characterized by a plurality of other surfaces that are intended to collectively operate together with the undersurface 111 and with the cap 190 or with the gasket-and-cap assembly 880 to minimize the stresses placed on any lead segment 206 (or segment of another medical device) that may be secured by the burr hole cover 100 after it is installed, and, for that matter, the stresses placed on other parts of the lead 203, such as the proximal portion where the lead exits the burr hole cover at the skull). Specifically, the top surface 140 provides features that allow the burr hole cover 100 to be used to affix the segment 206 of the proximal lead portion 210 in the burr hole cover while at the same time managing and minimizing stresses on the medical device (i.e., the lead 203 or other medical device), which stresses might affect the position of the distal end 214 of the medical device at the target area or compromise the integrity or functionality of the medical device.

In some embodiments, the material from which the retainer 110 and the cap 190 are formed is relatively rigid as compared to, for example, the material from which the gasket 170 is formed, although it will be appreciated that this difference in rigidity is not essential. In some embodiments, for example, the retainer 110 and the cap 190 may be formed from a polymer thermoplastic such as a poly-ether-ether-ketone material (e.g., PEEK) and the gasket 170 may be formed of a more resilient or pliable or lower durometer material such as a rubber or rubber-like material (e.g., silicone). Desirably all of the materials from which the components of the burr hole cover 100 are formed are biocompatible or at least non-toxic or of low toxicity.

The gasket 170 may be provided with a cylindrical projection or boss that has appearance of a first, smaller diameter cylinder 172 situated approximately concentrically over a second, larger diameter cylinder 174 with each cylinder defining an aperture 176 extending therethrough. A shoulder or gasket rim 178 is formed on the gasket 170 on the larger diameter cylinder 174 where a perimeter of the smaller diameter cylinder 172 ends and an edge of the larger diameter cylinder overlaps the smaller. The aperture 176 is designed to receive a plug 192 of the cap 190. In some embodiments, the gasket 170 is formed as a single piece by molding or using some other suitable process. In some embodiments, the gasket 170 is formed using a softer or more pliable material than the material from which the cap 190 (and/or the retainer 110) are formed, at least at the locations on the gasket 170 that may ultimately come into contact with the segment 206 of the proximal portion 210 of the lead 203 when the burr hole cover 100 is installed and the segment 206 is secured relative to the burr hole. A softer or more pliable material for the gasket 170 likely will present less stress to the segment 206 than would be the case if all of the surfaces with which the lead segment 206 comes into contact on the burr hole cover were surfaces formed of harder, less resilient material.

As described previously, the cap 190 may be configured to be provided to a user with the gasket 170 already situated around the plug 192 in a gasket-and-cap assembly 880. The cap 190 further may be provided with features that allow the cap 190 to be manipulated by a surgeon with some form of an installation tool, to make it easier to manipulate the cap 190 relative to the other components of the burr hole cover 100 and the lead 203 to be secured using the burr hole cover 100. The features may be a pair of apertures or recessions 194, 196 provided in a top or outwardly-extending surface of the cap 190 wherein the apertures or recessions 194, 196 are suitable for receiving the prongs of a forceps or tweezers or similar common surgical tool (e.g., forcep holes). Alternatively, the cap 190 may be designed for use with a custom installation tool, in which case the features provided in the cap 190 for facilitating installation will be suitable for use with, and perhaps unique to, the custom installation tool. (It will be appreciated that features to improve the ease with which the surgeon can manipulate the cap relative to the other components of the burr hole cover may also be relied upon to remove the cap, for example, in the process of removing or replacing a previously implanted lead that has been secured with the burr hole cover.)

In some embodiments, the cap 190 may be provided on an underside thereof with one or more guides (not shown) configured to receive a portion of the medical device (e.g., lead segment 206) that is fixated in the burr hole cover 100.

The cap 190 may be formed from a relatively rigid material as compared to the material from which the gasket 170 is formed. For example, the cap 190 may be formed from the same material as the retainer 110, such as PEEK. A rigid cap 190 may help to protect the lead once a lead segment 206 has been fixated in the burr hole cover 100 relative to the burr hole. For example, after the burr hole cover 100 has been installed with an implanted lead and the patient's scalp replaced (or a scalp substitute provided), a neurosurgeon or other physician may have a need to palpate the patient's scalp to locate the portion of the lead that extends proximally out of the burr hole cover 100. A relatively rigid cap 190 may guard against the lead becoming dislodged from the burr hole cover 100 during this process. After the burr hole cover 100 is installed and the scalp replaced over the burr hole cover site, a relatively rigid cap 190 may also protect the lead within the burr hole cover 100 from a surgeon's scalpel (for example, if the surgeon has to cut open the scalp again to replace a lead or other implanted medical device) and from palpations by a user, patient or caregiver at the burr hole location.

In some embodiments, the dimensions of the components of the burr hole cover 100 and particularly the retainer 110 will be provided to accommodate one or more common-sized burr holes. Burr holes are often drilled with special drill bits which are configured to form a fenestration in the cranial bone with predetermined approximate dimensions (e.g., a 14 mm diameter circular hole).

The retainer 110 may be provided so that the inner perimeter 109 defines a cap-receiving aperture 114 that circumscribes a circle that approximates the diameter of the burr hole. Desirably, the cap-receiving aperture 114 is generally centrally-situated in the retainer 110. The area provided in the cap-receiving aperture 114 may be thought of as corresponding to the amount of space in which a lead extending proximally out of the burr hole can be manipulated relative to the other features of the retainer 110 and the gasket-and-cap assembly 880 of the burr hole cover 100 (i.e., a working space in which the user can manipulate a lead and to select where to secure a lead segment 206 relative to the burr hole cover 100.).

The top surface 140 of the retainer 110 may include a center-facing portion surrounding the cap-receiving aperture 114. The center-facing portion near a bottom of the retainer may help to define a lower inner recessed area or lower ring 121 (see also FIGS. 7 and 10, and 11). In some embodiments, the lower ring 121 may be characterized by a lower rim 141 that will contact a portion of the cap 190 when the cap is inserted into the retainer 110. The lower rim 141 may be configured to receive the shoulder or gasket rim 178 of the gasket-and-cap assembly 880 when the burr hole cover 100 is installed. The lower rim 141 may serve to discourage the cap 190 from being unintentionally removed from the cap-receiving aperture 114 and when a lead segment 206 is situated in the burr hole cover 100, and the lower rim 141 may cooperate with the cap 190 (or gasket-and-cap assembly 880 as the case may be) to keep the lead segment 206 fixated in the burr hole cover relative to the burr hole.

The lower ring 121 may also be characterized by a width and a depth. The width of the lower ring 121, that is, the distance traversed by the lower ring 121 between its center-facing surface and an outwardly-facing surface, is the lower ring width 710 as illustrated in the bottom view of the retainer 110 shown in FIG. 7. The lower ring width 710 is also shown in the cross-sectional view of a retainer 110 shown in FIG. 10, together with the lower ring depth 1012 . . . .

The lower ring depth 1012 extends vertically (and will extend downwardly towards the brain when the retainer is being installed) from the undersurface 111 (see, e.g., FIGS. 1, 7 and 10) of the retainer 110. The lower ring 121 may be designed to seat interiorly of the burr hole formed in the patient, so that when the retainer 110 is installed, the lower ring 121 will extend at least partially into the burr hole traversing some or all of the distance between the outermost surface of the cranium and the innermost surface of the cranium (i.e., the surface of the cranial bone closest to the brain). The lower ring depth 1012 may be provided with a dimension that generally corresponds to the thickness of the average person's cranial bone in a given area of the skull.

Preferably, the lower ring depth 1012 will be selected so that when the burr hole cover 100 is completely installed, no component of the burr hole cover, including the retainer 110, the cap 190 (or the gasket 170 and the plug 192 of the cap, if a gasket is provided as a component) will extend further in towards the brain by a distance greater than the thickness of the cranial bone where the burr hole has been formed. The lower ring width 710 may be selected to be wide enough to provide stability to the lower ring 121 and the retainer 110 overall, but not so wide as to encroach too significantly upon the amount of user working space.

The lower ring 121 will contribute to keeping the overall profile of the burr hole cover 100 low relative to the surface of the patient's skull, and will help to anchor the retainer 110 during the time the retainer is being fastened to the cranial bone (e.g., using bone screws as is further described below). Alternatively or additionally, the lower ring 121 may be expected to discourage the retainer 110 from slipping away or becoming dislodged from the burr hole while the retainer 110 is being manipulated relative to the burr hole and the other components of the burr hole cover 100.

In some embodiments, the lower ring 121 may be provided with threads or ridges (not shown) on at least its outwardly-facing surface (that is, the lower ring surface that will face the cranial bone in the burr hole when the burr hole cover is installed). Such threads or ridges may encourage the retainer 110 to engage with a surface of the cranial bone exposed by the drilling of the burr hole and therefore further stabilize the retainer 110 relative to the burr hole.

In some embodiments, and for use in attaching the retainer 110 to the cranial bone, one or more outer recessed surfaces or areas 122 are provided in a upwardly sloping portion of the top surface 140 the retainer 110 (as slope is considered from the perspective of the outer perimeter 108 towards the inner perimeter 109). Each outer recessed area 122 may be configured to receive a bone-attaching element such as a bone screw (see, e.g., the heads 392 of the bone screws shown in FIG. 3 and the head 392 and the shank 1092 of the bone screw shown in FIG. 10). To accommodate the bone-attaching elements, each outer recessed area 122 may be provided with a bone-attaching aperture (see the apertures 712 shown in the bottom view of the retainer 110 shown in FIG. 7) Bone-attaching elements may be passed through the bone-attaching apertures to fasten the retainer 110 to the skull to minimize movement of the retainer 110 relative to the burr hole. In some embodiments, each outer recessed area 122 is provided so that when a screw is attached to the cranium, the screw heads 392 will not extend outwardly from the skull to an extent further than the extent to which the retainer 110 extends outwardly from the skull (see, e.g., the retainer 110, screw head 392 and screw shank 1092 illustrated in FIG. 10). It will be appreciated that an outer recessed area 122 may be provided so that it is configured to accept a bone-attaching element other than a screw, such as a pin.

When the retainer 110 is designed to be attached to the cranial bone via a bone-attaching element, it would be desirable for the material from which the retainer is formed to be resilient enough to allow the retainer to conform, at least partially, to the shape of the patient's skull in the area of the burr hole, so that after the retainer is attached, it is more or less flush with the skull.

In still other embodiments, the outer recessed areas 122 may be eliminated entirely and the retainer 110 securely located at the burr hole by other means, such as by attaching the undersurface 111 of the retainer 110 to the cranium 202 by an adhesive. In yet other embodiments, screw holes may be provided, but not in recessions. For example, screw holes may be provided in pads that extend outwardly from the retainer in a plane that will align approximately with a plane including the surface of the cranium when the retainer 110 is installed in a burr hole. In alternative embodiments, the undersurface 111 of the retainer 110 may be provided with a layer or portion that is configured to assist in conforming the retainer 110 to the cranial bone 202 in the area of the burr hole. In such embodiments, this layer or portion may be formed from a material that is more resilient or malleable than the material from which the rest of the retainer 110 is formed. For example, the layer or portion may be formed from silicone rubber or a shape-memory material and other parts of the retainer may be formed from a higher durometer material or from a polymer such as PEEK.

Features will now be described of embodiments of the burr hole cover 100 that are configured to, among other things, minimize the stresses and strains to which the medical device is subjected during and upon installation of the burr hole cover 100 to affix the medical device in the vicinity of the burr hole cover. More specifically, these features are provided at the point or points where a lead 203 (or other medical device) is intended to transition from the burr hole cover to elsewhere (such as the surface of the skull adjacent the burr hole and burr hole cover) to minimize the stresses and strains experienced by the device (such as the segment 206 of the proximal portion 210 of the lead 203) at such transition points.

For example, the burr hole cover 100 is provided with at least one retaining element (such as one or more grooves 132) configured, e.g., in terms of width, depth and length, so that the at least one retaining element will resist lateral or longitudinal movement of the lead segment 206, when a first portion of the lead segment 206 is situated within that retaining element. In addition, the burr hole cover 100 is configured to press a second portion of the lead segment 206 between the retainer 110 and the cap 190 at the lower ring of the retainer when the lead segment 206 is situated in a groove and the cap is pushed into the retainer.

Thus, the burr hole cover 100 is provided with features, and its components are intended to be arranged in such a way so as to minimize stresses and strains on most portions of a lead 203 most of the time, except for one segment 206 of the lead that is secured in the burr hole cover, for example, in a portion of a groove 132 and pressed between the cap 190 and the retainer 110 at the retainer lower ring 121, by press fitting or compression fit. In this manner, the burr hole cover 100 allows the lead 203 to be secured relative to the lead distal portion 212 implanted in the brain, on the one hand, and the lead proximal portion 210 extending out of the burr hole, on the other hand, without the lead acutely or chronically encountering any sharp edges or other severe transitions (e.g., from one material of the burr hole cover to another, or from the burr hole cover to the surface of the skull) that potentially may be hazardous to maintaining the integrity of the lead (or an intended function of the lead or its associated electrodes or other sensors or tissue modulators).

The features of embodiments of the burr hole cover described herein result in a burr hole cover with: (1) a small number of components, any one of which can be managed and manipulated relatively easily by a surgeon; (2) a desirable low profile to discourage the patient from fiddling or fussing with the burr hole cover and to minimize the extent to which the burr hole cover can be perceived by others after installation (e.g., to minimize the extent to which the device appears as a bulge under the scalp (i.e., an aesthetics-enhancing feature); (3) a secure enough fixation of the lead as between the lead portion(s) at the target(s) in the brain and the lead portion extending away from the brain and proximally of the burr hole that is suitable and sufficient for many applications or intended uses, such as one in which an electrode-bearing deep brain lead is used for diagnosing and/or treating epilepsy; (4) lead-contacting surfaces that facilitate smooth transitions (e.g., from burr hole cover component to burr hole cover component or from burr hole cover component to skull), to minimize the risk that the lead will break or otherwise have its function compromised by a mechanical stress or strain at the juncture of the lead and the burr hole cover; and (5) one or more components or features of components that allow better control over the extent and degree to which the portion of a lead constrained in the burr hole cover is deformed when the burr hole cover is used to secure a lead portion.

Figure 7:
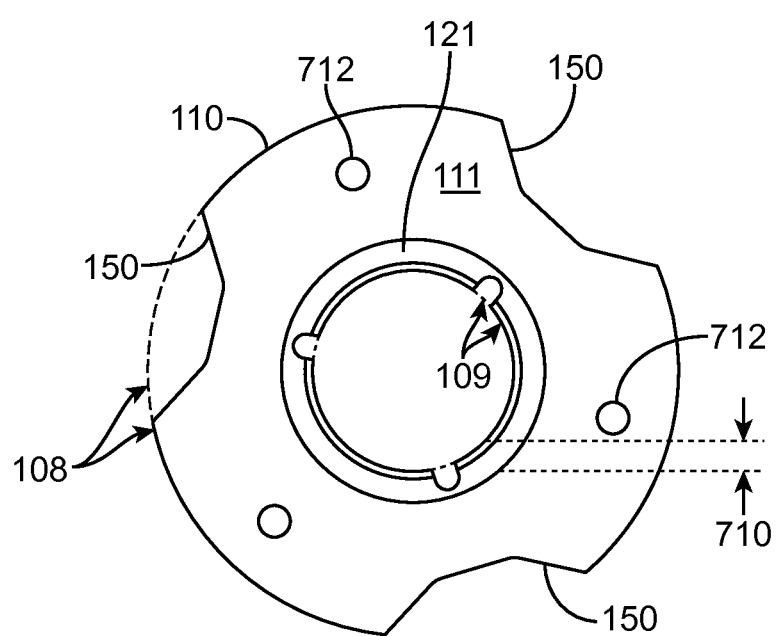
FIG. 7 is a bottom plan view of a retainer according to a burr hole cover embodiment.

In some embodiments, and as previously mentioned, the retainer 110 is characterized by a multifaceted top surface 140 as shown in the perspective view of FIG. 1 and in FIGS. 2A-2B, and FIGS. 4 and 8-11 which is generally opposite the undersurface 111 (e.g., shown in FIG. 7). The top surface 140 extends between an outer perimeter 108 and an inner perimeter 109 which helps define a cap-receiving aperture 114 and space in which to manipulate the lead 203 while the surgeon is deciding where in the retainer 110 to situate the lead and before the cap 190 is pushed into the retainer.

The top surface 140 may vary in height (or depth) between the outer perimeter 108 and the inner perimeter 109, such that the top surface is configured to have little height at the outer perimeter then increase in height on an upward slope to its greatest height towards the cap-receiving aperture, and then transition to a downward slope that continues to the lower ring 121. When the retainer 110 is installed, the greatest height of the retainer 110 may correspond to the point of the installed burr hole cover with the highest profile.

Figure 3:
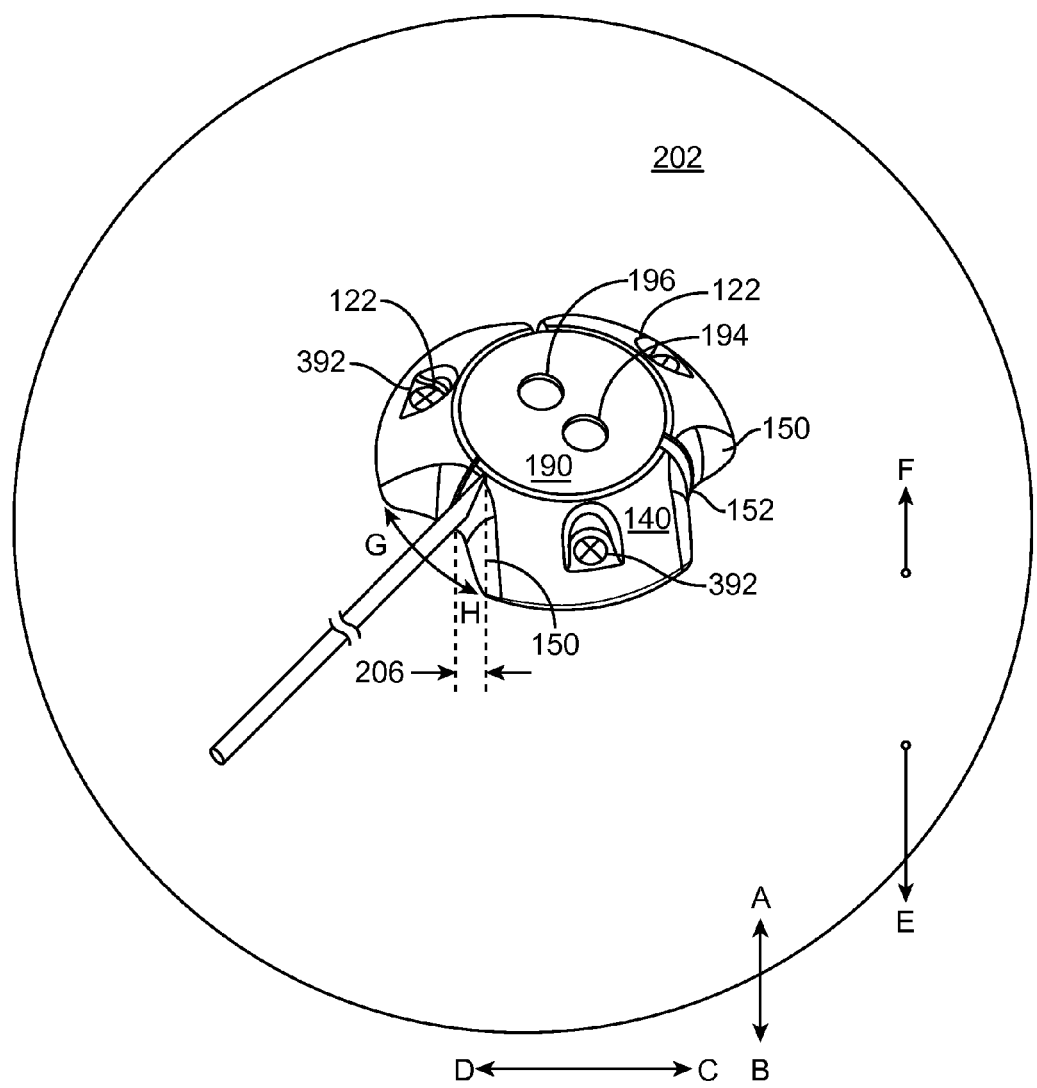
FIG. 3 is a perspective view illustrating a portion of a lead extending proximally of a burr hole cover, according to an embodiment/

Directions which may be referred to herein are illustrated in FIG. 3 relative to a burr hole cover 100 installed in a burr hole in a patient's cranium 202: the vertical direction, namely, with arrows A and B, and the horizontal direction, namely with arrows C and D; the distal direction, with arrow E; the proximal direction, with arrow F; and a range of motion of a lead portion after it exits a retaining element 132 (e.g., a groove in FIG. 1) in the retainer 110, namely, a range of motion indicated by the arrows G and H. It will be appreciated that a given patient's skull will be characterized by different radii of curvature depending on where a burr hole is located, so that the "vertical" and "horizontal" directions primarily have meaning relative to each other (i.e., the horizontal being a direction corresponding to a plane extending perpendicular to a plane that contains the vertical) rather than relative to a top and bottom or right to left.

In some embodiments, and as previously described, the center-facing part of the top surface 140 is provided with a lower ring 121 that has a depth and a width and that is designed so that, when the burr hole cover 100 is installed, the lower ring 121 will at least partially traverse the thickness of the cranial bone through which the burr hole has been formed. In other embodiments, the retainer 110 may be configured so that the center-facing part of the retainer top surface 140 defines a lower edge (not shown in the figures) that is intended to be approximately flush with the outermost surface of the cranial bone when the retainer 110 is placed at the burr hole location.

In some embodiments, where the retainer top surface transitions from an upward slope to a downward slope (at or near the greatest height of the retainer), an upper inner recessed area 134 is provided to receive a portion of the cap 190. It will be appreciated that while parts of the retainer top surface 140 may be separately described herein, the entire retainer 110 may be formed contiguously in a single integrated unit (e.g., by forming the retainer by injection molding or some other molding or casting or stamping process).

As is described above, in some embodiments the height or depth of the retainer in the portion characterized by the upwardly-sloping surface increases from the outer perimeter 108 to the inner perimeter 109, such that the retainer 110 is thicker (or taller) in the location of the cap-receiving aperture 114 than it is in the location of the outer perimeter 108. It may be desirable to form the retainer 110 so that the thickness (or height) of the retainer near the outer perimeter 108 is as thin (or low) as feasible, for reasons including, once the burr hole cover 100 is installed, having the lead portion 206 that exits the burr hole cover 100 be as close as practicable to the surface of the cranium 202 and in the interest of maintaining an overall low profile for the burr hole cover 100 and associated lead 203. In part owing to the upward slope of the top surface 140, after the burr hole cover 100 is completely installed (that is, with the gasket-and-cap assembly 880 positioned in the retainer to secure, for example, a portion of a lead 206), the overall appearance of the burr hole cover 100 will be approximately dome like (see, e.g., FIGS. 2 and 3).

In still other embodiments, it may be desirable to form the retainer 110 so that any upward slope is controlled to ensure that the retainer is thick enough (or tall enough) so that there will be a gradual angle of transition wherever the lead 203 may exits the burr hole cover 100 at an outer end 152 of a groove 132. This gradual angle may cooperate with a cut-out 150 that is formed at each groove outer end 152 in order to discourage unwanted stressing of the lead both during and after the burr hole cover is installed.

More particularly, each groove 132 may be associated with a cut-out 150 at an outer end 152 thereof that is configured to receive a segment 206 of a lead 203 (see FIG. 2) or other medical instrument towards the outer perimeter 108 of the retainer 110. In the embodiments shown in the figures here, there are three cut-outs 150 in each retainer 110, and thus the retainer 110 appears to be divided into three lobes that are approximately equidistant from each other. It will be appreciated that more or fewer than three cut-outs 150 may be provided in a retainer 110 in order to allow more or fewer locations in which to secure a lead segment 206 in the burr hole cover 100. It further will be appreciated that the layout of the cut-outs 150 may be different, for example, they may not be provided equidistant from each other in the retainer 110.

Desirably, the horizontal length 131 of each groove 132 (as measured from an inner groove edge 154 (at the groove end closest to the retainer inner perimeter 109) and the outer groove end 152 is selected to be long enough to allow a sufficient segment 206 of the lead 203 to be retained in the groove to allow secure retention, which retention may be supplemented by the insertion of the gasket-and-cap assembly 880 into the retainer 110. Similarly, the depth 133 of each groove 132 (as measured from the top surface 140 down to the portion of the groove that is most proximate to the undersurface 111 of the retainer), is selected to be deep enough to allow the lead segment 206 to be securely retained in the groove 132.

In some embodiments, and referring now to FIGS. 4A and 4B, as well as to FIG. 1, each groove 132 might be configured to have a width 415 (for example, a diameter if the groove is provided generally in the form of one half of a cylinder) that is slightly less than the diameter 420 of the lead 203 (or other medical device) with which the burr hole cover 100 is intended to be used. Thus, when a user presses the lead segment 206 into a groove 132, the slightly smaller diameter of the groove 132 will offer some resistance initially. However, once the lead segment 206 is situated in the groove, the differences in diameters between the lead and the groove will tend to resist forces that otherwise might cause the lead segment to pop out or otherwise come loose of the groove.

Figure 6:
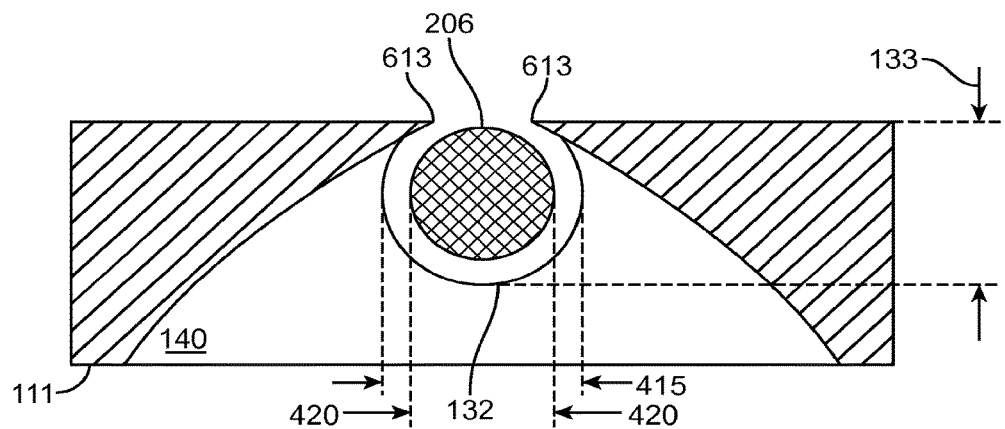
FIG. 6 is a cross-sectional view of a groove having a segment of a proximal portion of a lead disposed therein and an overlip provided in the retainer at the groove according to a burr hole cover embodiment.
Figure 5:
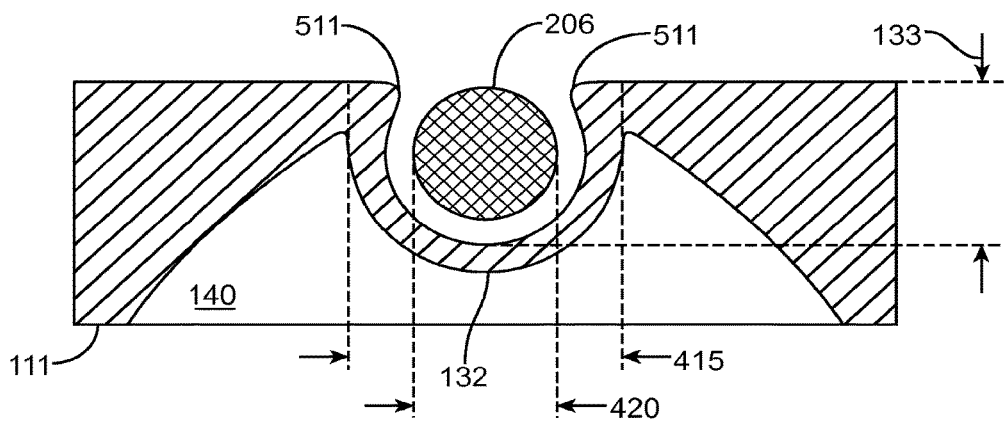
FIG. 5 is a cross-sectional view of a groove of a retainer provided with a groove insert according to a burr hole cover embodiment.

In other embodiments, and referring now to FIGS. 5 and 6, a groove 132 may be formed so that it will provide a snug fit for the lead with which the burr hole cover 100 is intended to be used, but not so that it is characterized by a groove width 415 (e.g., a groove diameter) that is smaller than the diameter 420 of the lead. In one such embodiment, the groove(s) 132 may be provided with an overlip 613 that extends over the space in which the lead segment 206 is intended to be situated. In these embodiments, the lead segment 206 may deform slightly as it is inserted into the groove 132 in order to get past the overlip 613. In these embodiments, the overlip 613 may help retain the lead segment 206 in the groove 132 regardless of whether the fit of the lead segment 206 in the groove 132 is also a friction or interference or press fit. In other words, the overlip 613 will resist any forces that otherwise would encourage the lead to pop out of the groove even if lead segment 206 is not that closely matched in diameter to the diameter of the groove. In these embodiments, the overlip 613 may allow the burr hole cover 100 to be used with leads or other devices having a range of diameters than would a burr hole cover that relies exclusively on the groove diameter being slightly less than the lead diameter in order to retain the lead in the groove.

In yet further embodiments, either or both of the groove width 415 and the groove depth 133 may be configured to be greater than the dimension (e.g., the diameter) of the lead or other medical device with which the burr hole cover 100 is intended to be used, and the lead segment 206 will be retained in the groove 132 by virtue of the gasket 170 compressing the lead segment 206 after the gasket-and-cap assembly 880 has been inserted into the cap-receiving aperture 114. In these embodiments, contact between the lead segment 206 and the gasket-and-cap assembly 880 may be kept to a minimum (and therefore stresses on the lead may be kept to a minimum) as the gasket-and-cap assembly 880 is being inserted into the cap-receiving aperture 114. More specifically, the gasket 170 will have insubstantial contact with and will not engage the lead segment 206 until after the gasket-and-cap assembly 880 has been snugly fit into the cap-receiving aperture 114. This feature may discourage the distal end of the lead from being dislodged from the implant site during installation of the burr hole cover 100.

Each groove 132 may be provided so that it is characterized by a generally consistent depth 133 along the horizontal length 131 (i.e., across the top surface 140 when measured relative to the undersurface 111 as the groove extends from the inner perimeter 109 of the retainer in the direction of its corresponding cut-out 150 and the outer perimeter 108 of the retainer 110). Thus, any lead segment 206 that is placed within any of the grooves 132 will remain at the approximately the same height above the undersurface 111 of the retainer 110 when it is situated within the groove. Alternatively, one or more of the grooves 132 may be provided in the retainer so that the groove is characterized by an incline when viewed from the perspective of the outer perimeter 108, such that the groove depth 133, relative to the undersurface 111 and along the horizontal groove length 131, is deeper at the inner perimeter 109 than it is at the point where the groove 132 transitions into the cut-out In some embodiments, each groove 132 may be provided so that it not only extends across an upwardly sloping part of the top surface 140, but also continues vertically down through to a center-facing part of the top surface and out through the undersurface 111 (see FIG. 7). In these embodiments, a groove 132 can be used to capture the lead segment 206 both in the vertical and horizontal directions (see FIG. 3 and the arrows A and B and the arrows C and D, respectively).

In some embodiments, a lead exit feature of the retainer 110 includes both a groove 132 and a cut-out 152, where at a groove end 152 towards the outer perimeter 108, each groove 132 widens to allow more range of movement for any lead portion proximal of the lead segment 206 placed within the groove as that proximal portion exits the burr hole cover 100. In the illustrated embodiments, each groove end 152 opens into a generally V-shaped cut-out 150, so that a lead portion 206 placed within a groove 132 generally will have a range of motion as indicated by the arrows G and H in FIG. 3. The transition between the lead-retaining portion of the groove 132 and the groove end 152 may be configured to have gentle (as opposed to sharp) curves and/or no sharp edges, to minimize the stress experienced by the lead as it exits the groove 132. Similarly, the transition between each groove end 152 and its corresponding cut-out 150 will be provided free of sharp edges or defects to avoid unduly stressing the lead as it leaves the burr hole cover 100. It will be appreciated that shapes for the cut-outs 150 other than a V-shape may also be suitable to permit the proximally-extending lead portion to move relatively unencumbered and at gentle angles just proximal of a groove. Such shapes include elliptical, round, or some complex combination of geometrical shapes.

As previously described, the retainer 110 may be formed of a different material than one or more of the other components of the burr hole cover 100. For example, the retainer 110 may be formed of a relatively hard material, such as polyether ether ketone (PEEK). When the retainer 110 has been formed of a relatively rigid material, it may be desirable to supplement the retainer 110 in each exit-defining surface 130 in the area of one or more groove 132 with a more resilient and/or smoother material in order to further reduce the stress any lead portion secured in the groove 132 is likely to experience. This might be accomplished for example (and referring now to FIG. 6) by fitting each groove with an insert 511 formed from a softer or more supple or flexible material, such as silicone rubber. Alternatively, a softer material may be overlaid on each groove in the manufacturing process.

As previously described, the retainer 110 may be provided with an upper inner recessed area 134 for receiving one portion of the gasket-and-cap assembly 880, namely, a lip of the gasket-and-cap assembly 880 that is free of the gasket 170 and which is intended to rest against the upper inner recessed area 134 when the burr hole cover 100 is fully installed. The center-facing portion of the retainer top surface 140 further may be provided with a downward slope or downwardly-sloping portion that is configured to contact substantially all of an outer circumference of the gasket 170 when the burr hole cover 100 is fully installed, save for any portions of the retainer top surface 140 and the cap gasket 170 that may press against the lead segment 206 to help retain the lead in the burr hole cover 100.

Referring now primarily to FIGS. 2A-2B, FIGS. 3, 8 and 9, a method of using a burr hole cover according to some embodiments will be described. A lead 203 (or other medical instrument such as a catheter) may be partially implanted in the patient so that a distal portion of the lead 212 (or other medical instrument) extends distally from the burr hole towards and/or into the patient's brain (see, e.g., the direction represented by the arrow E in FIG. 3) and a proximal portion 210 of the lead (or other medical instrument) extends proximally from the burr hole away from the patient's brain (see, e.g., the direction represented by the arrow F in FIG. 3).

By the time the lead is implanted, the retainer 110 may previously have been situated at the location of the burr hole so that the lead 203 is passing through the cap-receiving aperture 114. If the retainer 110 is provided with one or more bone-attaching apertures 712 each configured to receive a bone-attaching element such as a bone screw, the retainer 110 can be secured to the patient's cranium 202 using the bone screw(s). Depending on the configuration of the retainer 110, it may be secured to the cranium 202 by other or additional means, such as an adhesive. Alternatively, if the retainer 110 is provided with a feature for slipping the retainer 110 around a lead 203 (e.g., a slit provided in the retainer (not shown in the figures)), then the retainer 110 can be situated at the location of the burr hole even after the lead has been implanted and a portion of the implanted lead is extending proximally out of the burr hole. When the user is placing the retainer 110 in the burr hole, the user can situate the retainer 110 so that any retaining elements or grooves 132 are oriented in a particular direction relative to the patient's cranium and any other implanted or external device to which the implanted lead 203 is to be connected.

Depending on where the user wants the proximal portion 210 of the lead 203 to ultimately be located (e.g., dressed out of the burr hole in an anterior direction (such as towards the patient's nose) or dressed out of the burr hole in a posterior direction (such as towards the patient's back)), the user can selected one of the grooves 132 in which to situate the lead segment 206.

When the surgeon is ready to position the lead segment 206 in the retainer 110, if the lead 203 has been provided with a stiffener such as a stylet which has not yet been removed, then the stiffener desirably is removed at this point. Then, once the user has selected a groove 132 to use, the surgeon may press a proximal portion 210 of the lead at the burr hole, i.e., lead segment 206, down into one of the grooves 132. If the top surface 140 of the retainer 110 is provided with a rounded curvature as it transitions from an upward slope to a downward slope towards the cap-receiving aperture 114 (for example, at the transition between an upper inner recessed area 134 and another part of the top surface) and the retainer is provided with grooves 132 that extend both vertically and horizontally, then when the user situates the lead segment 206 in the groove, the portion of the lead extending distally of the lead segment 206 will follow the rounded curvature. Thus, rather than having the lead bend in the retainer at a sharp 90 degree angle, the lead segment 206 will traverse the groove more gently or gradually. This feature avoids a sharp bend in the lead segment 206 from the vertical to the horizontal may further discourage compromising the integrity or function of the lead (e.g., by avoiding kinking or breaking any conductors that might be provided in the lead or other medical device).

When the lead segment 206 is positioned in one of the grooves 132, a lead portion 210 extending proximally of the lead segment 206 is free to move in the direction indicated by the arrows G and H in FIG. 3. The cut-outs 150 allow the horizontal length 131 of each groove 132 to be relatively short and the groove depth 133 (at least along the horizontal length 131 of the groove) to be relatively deep, so as to keep the lead segment 206 that is constrained in the groove 132 relatively small as compared to the overall length of the lead.

As previously described, both the groove ends 152 and the cut-outs 150 desirably are free of sharp edges or other obstacles that may stress portions of the lead that contact the burr hole cover 100 before, during or after the burr hole cover 100 is installed, particularly a portion of the lead that extends proximally of the burr hole cover from the lead segment 206 that is fixated as a result of installing the burr hole cover. Thus, these methods of installing the burr hole cover according to embodiments which allow relatively free lateral movement of the lead proximal of a given groove are believed likely to minimize the stresses and strains on the proximally-extending portion of the lead at the groove, discourage the proximally-extending lead portion from engaging with other surfaces of the retainer, and prevent cuts and/or breaks in the lead (such as in an outer insulation layer provided in the lead) due to the lead encountering sharp angles, edges or other defects. These methods will also minimize the likelihood that the lead will be dislodged or will migrate from the site(s) at which a distal end or ends 214 of the lead 203 have been implanted, by virtue of retaining the lead segment 206 in one of the grooves 132 and, in some embodiments, a compressive force applied to the lead segment 206 by the gasket-and-cap assembly 880 (i.e., when a groove 132 alone is not solely responsible for retaining the lead segment 206 in the burr hole cover 100).

Once the user has situated the lead segment 206 in a desired groove 132, if the lead 203 was implanted with a stylet and the stylet has not yet been removed from the lead, then the user may retract and remove any stylet from the lead 203 at this point.

Once the lead segment 206 is situated in a groove 132, the user may orient the gasket-and-cap assembly 880 so that the plug 192 is oriented over the cap-receiving aperture 114 of the retainer 110 and then press the gasket-and-cap assembly 880 into the retainer 110. The material from which the cap 190 and/or the gasket 170 are formed may be clear or at least opaque, so that as the gasket-and-cap assembly 880 is manipulated relative to the retainer 110, the user will be able to perceive the lead segment 206 and the portion of the lead extending distally of the lead segment 206 notwithstanding the presence of the gasket-and-cap assembly 880.

When the user introduces the gasket-and-cap assembly 880 into the retainer 110, a portion of the gasket 170 likely will contact the lead segment 206, so that the lead segment is further secured between the groove and the gasket. (The extent of the role the gasket- and cap assembly 180 plays in retaining the lead segment 206 in the burr hole cover 100 will depend in significant part on the configuration of the grooves 132 as described above.) If the gasket 170 does contact the lead during or after the gasket-and-cap assembly 880 is inserted into the retainer 110, and the gasket 170 is formed from a material that is softer than the material from which either or both of the retainer and cap are formed, for example, a material that is similar in consistency or flexibility to that from which the lead (or other medical device) is formed, then the user's action in pressing the gasket-and-cap assembly 880 into the cap-receiving aperture 114 of the retainer 110 should result in very little stress or strain on the lead segment 206.

Optionally, the user can further dress a portion of the lead extending proximally of the groove 132 on the patient's skull by, for example, tacking the lead down to the cranial bone with a staple or suture or the like. This may be accomplished before or after the burr hole cover 100 is completely installed (i.e., before or after the gasket-and-cap assembly 880 has been pressed into the retainer 110). More often than not, however, this further lead dressing will occur after the surgeon has finished installing the burr hole cover. The surgeon may coil up the remaining proximal portion of the lead and replace the patient's scalp over the surgical field, with the intention of connecting a proximal end of the lead (not shown) to external monitoring equipment or a test stimulator or to another implanted medical device, such as an implanted neurostimulator.

Referring now to FIGS. 12-18, alternative embodiments of a burr hole cover will be described. In FIGS. 12A-12B, a burr hole cover 1200 comprises a retainer 1210 and a cap 1290.

Figure 8:
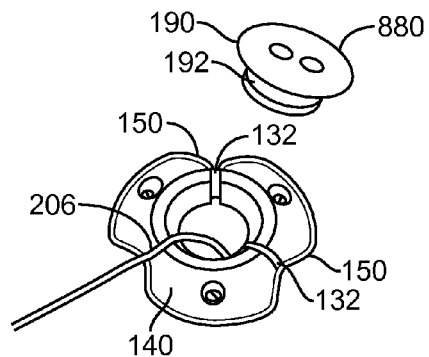
FIG. 8 and FIG. 9 each is a schematic view illustrating a method of using of a burr hole cover according to an embodiment in order to secure a segment of a medical device relative to the burr hole cover.

The cap 1290 may comprise an assembly of one or more components, such as the gasket-and-cap assembly 880 described with reference to FIG. 8. Alternatively, the cap 1290 may be formed as a unitary piece. Such a unitary piece may be easier and less expensive to manufacture than would a multi-component cap assembly.

The cap or cap assembly may be provided with a uniform material. The material may be relatively rigid as was the material of the cap 190 in some of the embodiments described with reference to FIGS. 1-11 above, such as a plastic or polymer (e.g., PEEK). Alternatively, the material may be relatively pliant as was the material of the gasket 170 in some of the embodiments described with reference to FIGS. 1-11 (e.g., silicone rubber). A pliant material for the cap 1290 may be desirable, for example, because it will not stress the lead segment 206 as much as might a rigid cap. In some circumstances, specifying a pliant material for the cap may result in economies of manufacture. For example, silicone may be less expensive than is a polymer such as PEEK, especially if the polymer is a proprietary material. Similarly, a pliant material may be easier to work with or test during the manufacturing process and by a user during the process of installing the burr hole cover 1200. Additionally, a pliant or resilient material may be more comfortable to the patient (for example, if the patient runs a finger over the location of an installed burr hole cover, it may be more pleasant to encounter a more malleable cap than it would be to encounter a more rigid cap).

The material used to form the cap 1290 may be clear or at least opaque, so that the interior of the retainer and the lead segment 206 and distally-extending portion 212 of the lead 203 can be perceived by the user as the cap is being installed in the retainer 1210.

The cap 1290 may be provided with features to make it easier to manipulate the cap relative to the retainer 1210 while the burr hole cover 1200 is being installed (or, for that matter, removed), such as cap recessions 1294 and 1296.

Figure 12A:
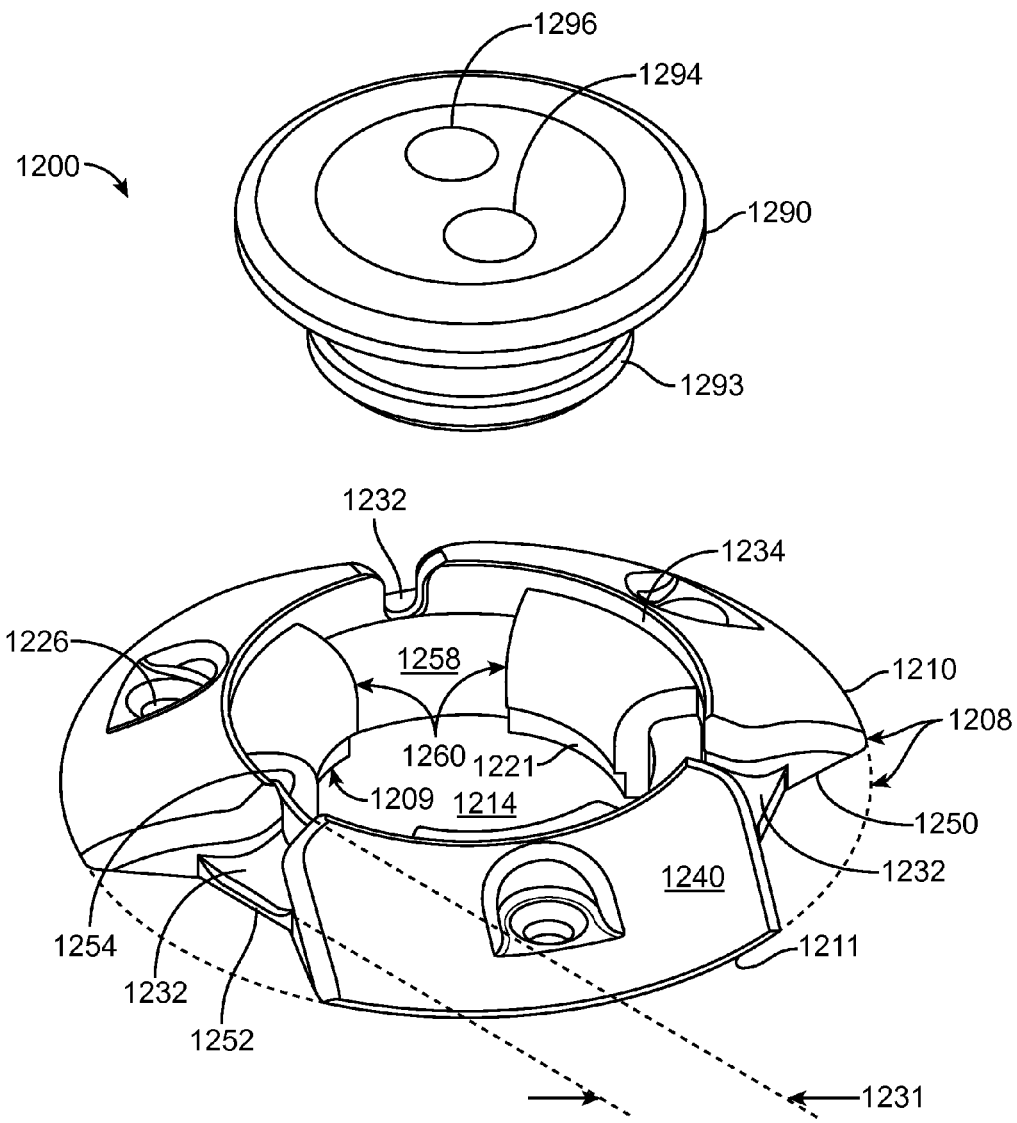
FIG. 12A is an exploded perspective view a burr hole cover according to an embodiment.
Figure 12B:
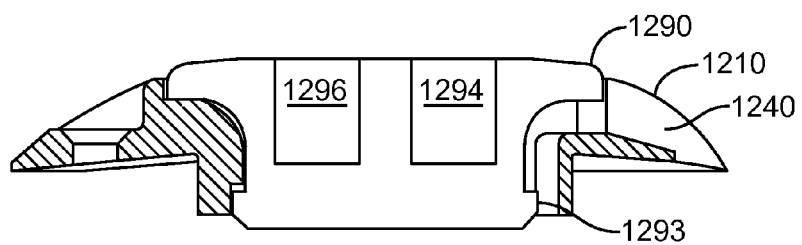
FIG. 12B is a cross-sectional view of a burr hole cover, with the cap component assembled with retainer component (without a medical device or lead secured therein).
Figure 13:
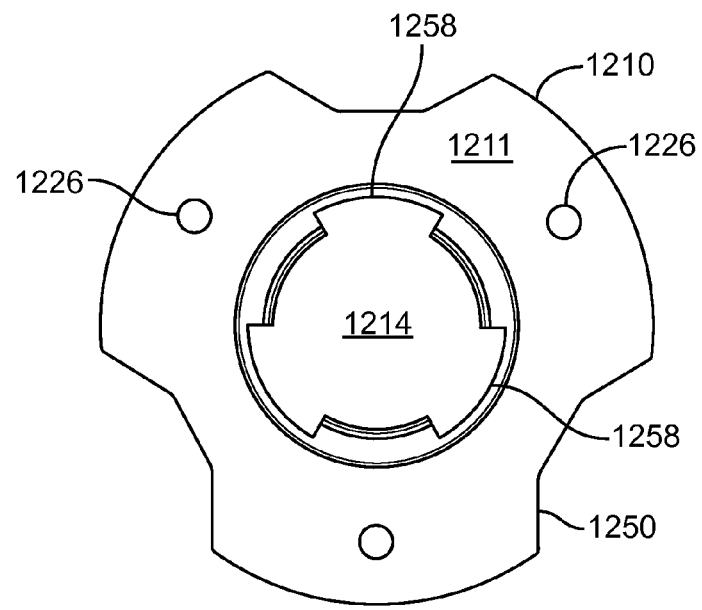
FIG. 13 is a bottom plan view of a retainer of a burr hole cover according to an embodiment.
Figure 14:
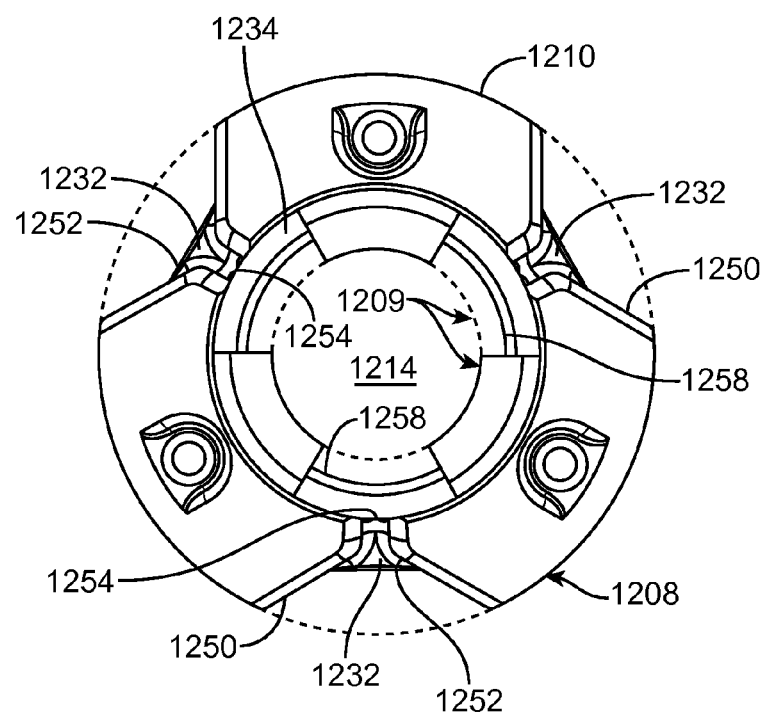
FIG. 14 is a top plan view of the retainer of FIG. 13.

Similarly to the embodiments described with reference to FIGS. 1-11, and referring now to FIG. 12A, a multifaceted top surface 1240 of the retainer 1210 may extend from an outer perimeter 1208 to an inner perimeter 1209. Opposite the top surface 1240 is an undersurface 1211 (see also FIG. 13). The top surface 1240 may include a center-facing portion surrounding a cap-receiving aperture 1214. The center-facing portion near a bottom of the retainer may help to define a lower inner recessed area or lower ring 1221, similar to the lower ring 121 described with reference to FIGS. 1-11. In some embodiments, a portion of the cap 1290 will fit within the lower ring 1221 when the cap is inserted into the retainer 1210. For example, the lower ring 1221 may be configured to receive the cap shoulder 1293 when the burr hole cover 100 is installed. The lower ring 1221 may serve to discourage the cap 1290 from being unintentionally removed from the cap-receiving aperture 1214 and when a lead segment 206 is situated in the burr hole cover 1200, and the lower ring 1221 may cooperate with the cap 1290 to keep the lead segment 206 fixated between the retainer 1210 and the cap 1290 relative to the burr hole.

Figure 15A:
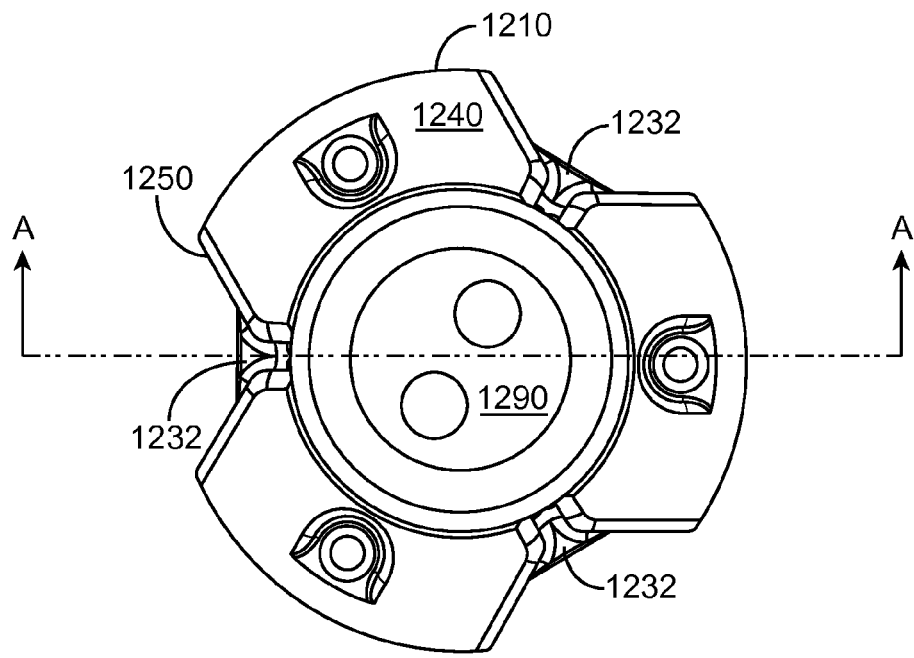
FIG. 15A is a top plan view of an assembled burr hole cover according to an embodiment.
Figure 15B:
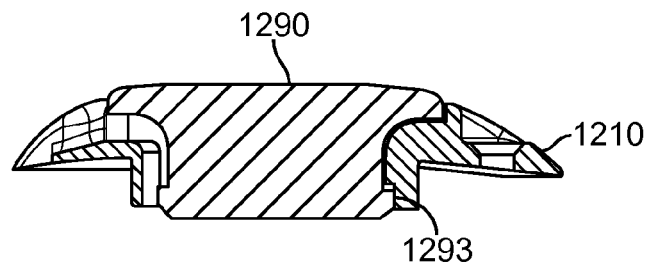
FIG. 15B is a side elevational view of the burr hole cover of FIG. 15A taken along the line A-A.
Figure 16:
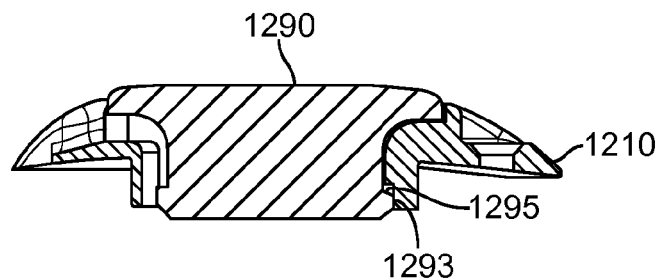
FIG. 16 is a side-elevational view of an assembled burr hole cover with an alternative embodiment of a cap.
Figure 17:
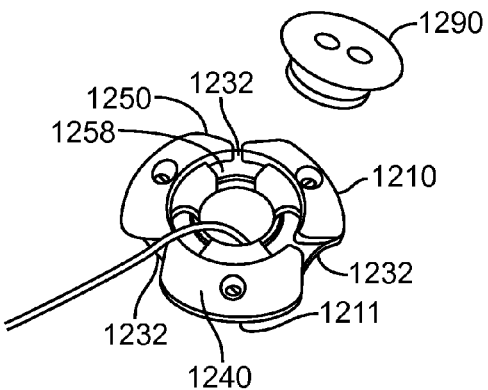
FIG. 17 and FIG. 18 each is a schematic view illustrating a method of using a burr hole cover according to an embodiment in order to secure a segment of a medical device relative to the burr hole.
Figure 18:
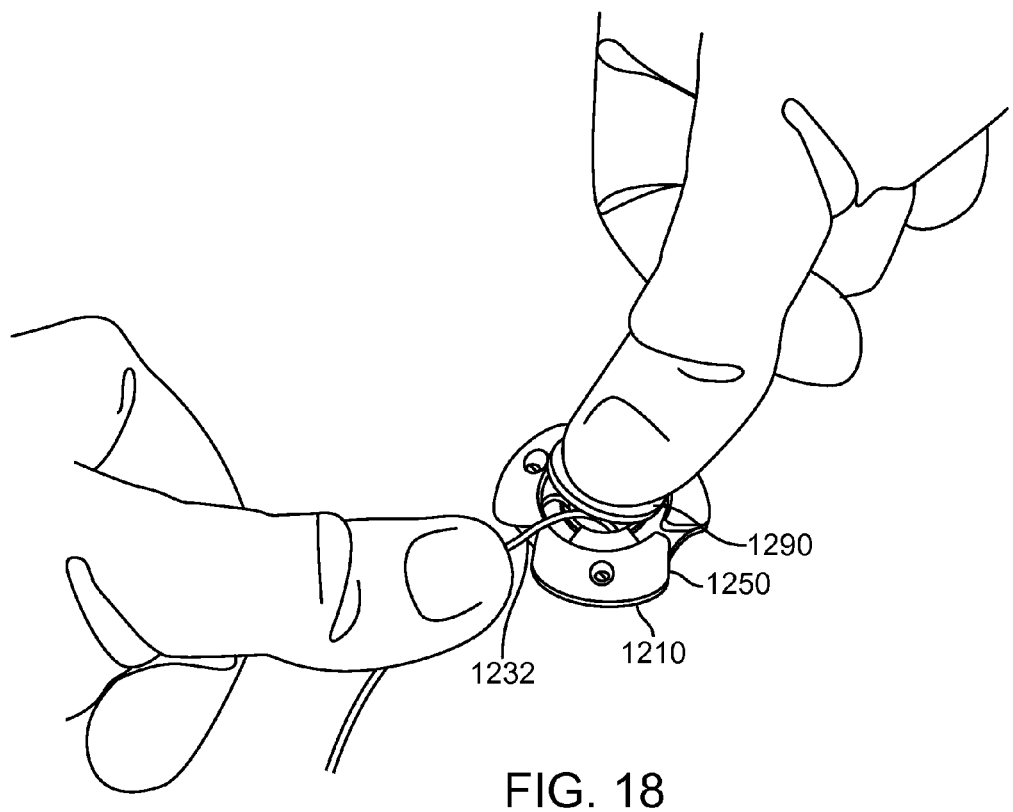

As best seen in FIG. 15B, the cap shoulder may be provided with an approximately right angle where the cap shoulder is intended to fit in the lower ring 1221 of the retainer 1210. Alternatively, the cap shoulder 1293 may be provided with a chamfered edge 1295, as shown in FIG. 16. The chamfered edge 1295 may make it easier to pull the cap 1290 out of the retainer 1210 should the need arise to do this.

Similar to the retainer 110 described with reference to FIGS. 1-11, the retainer 1210 may be characterized by a varying height as considered from the outer perimeter 1208 towards the inner perimeter 1209, with an upward slope towards the cap-receiving aperture, a peak height followed by a rounded transition to a downward slope where the top surface 1240 faces the cap-receiving aperture 1214. Like the embodiments shown in FIGS. 1-11, the retainer 1210 may be characterized by a plurality of retaining elements 1232 (three grooves 1232 in FIGS. 12A, 14, 15A and 18).

Each groove 1232 may have a first end 1252 near the retainer outer perimeter 1208 and a second end 1254 near the inner perimeter 1209. A groove length 1231 corresponds to the distance along the horizontal direction between the first groove end 1252 and the second groove end 1254.

As in the embodiments described with reference to FIGS. 1-11, in the area of each groove first end 1252, a cut-out 1250 is provided in the retainer top surface 1240. Each cut-out 1250 is configured to provide a range of motion, at least in a plane roughly parallel to the plane of the cranium, for a proximally-extending lead portion 210 when a segment 206 of the lead is situated in an associated groove 1232 and pressed between the cap 1290 and the retainer 1210 (e.g., between the cap shoulder 1293 and the retainer lower ring 1221).

Additionally, in the area of each groove second end 1254, a channel 1258 is provided. Each channel 1258 is indented in the top surface 1240 in a center-facing portion thereof and extends from the highest point of the top surface 1240 (e.g., greatest height of the top surface) to the undersurface 1211. Each channel is characterized by a channel width 1260. The indentation may be measured as a channel depth. The channel width 1260 may vary across the channel. For example, a channel 1258 may be wider towards the top of the retainer 1210 than it is near the bottom (towards the undersurface 1211) of the retainer 1211. The channels 1258 may be provided so that, once a user has situated a lead segment 206 in a groove 1232, the lead segment 206 will tend to stay in the groove as the cap 1290 is being pressed into the cap-receiving aperture 1214, and the distally-extending portion of the lead segment 206 will be less likely to be pinched between the cap 1290 and the retainer 1210 in an area other than in the area of a channel 1258 and its associated groove 1232. It will be apparent that channels with different configurations, including different depths and widths, may be provided according to embodiments in order to achieve the same objective of preventing undesired pinching of the lead as the burr hole cover is being installed.

As was the case with the embodiments described with reference to FIGS. 1-11, the retainer top surface 1240 may be provided with an upper inner recessed area 1234 which is configured to receive a surface of the cap 1290, so that when the cap 1290 is situated in the retainer 1210, the profile of the assembled cap-and-retainer will be no greater or only slightly greater than the profile of the installed retainer alone. The upper inner recessed area 1234 may be provided with rounded contours, to minimize the stresses placed on a lead segment 206 as it transitions from a channel 1258 through a corresponding groove 1232 and out through a corresponding cut-out 1250.

Similarly to the embodiments described with reference to FIGS. 1-11, a groove length 1231 is selected to be long enough to allow a sufficient segment 206 of the lead 203 to be retained in the groove to allow secure retention, which retention may be supplemented by the insertion of the cap 1290 into the retainer 1210. The depth of each groove 1232 (as measured from the top surface 1240 down to the portion of the groove that is most proximate to the undersurface 1211 of the retainer), is selected to be deep enough to allow the lead segment 206 to be securely retained in the groove. A groove 1232 may be characterized by an upward slope (as perceived from the outer perimeter 1208 towards the inner perimeter 1209) and therefore a varying depth along its horizontal length. For example, a groove 1232 may be provided so that it is deeper at the inner perimeter 1209 than it is at the point where the groove 1232 transitions into its corresponding cut-out 1250.

The width of a groove 1232 may be selected to be similar to that of the width (e.g., a diameter) of a lead or other medical device with which the burr hole cover 1200 is to be used. Alternatively, a groove width may be provided so that it is slightly smaller than the diameter of the lead or medical device so that when a portion of the medical device or lead segment is situated in the groove, it will be likely to remain there by reason of a friction- or press-fit.

As with the embodiments of FIGS. 1-11, the lower inner recessed area or lower ring 1221 may be designed with a diameter suitable to allow the lower ring to seat within the burr hole when the retainer 1210 is installed, to keep the retainer 1210 in place and to help to anchor the burr hole cover 1200 when installation is complete. Desirably, however, the lower ring 1221 width or thickness should not be so wide as to encroach too significantly upon the amount space in the retainer cap-receiving aperture in which the user has to maneuver the lead 203 when deciding in which groove to situate the lead segment 206.

Preferably, the components of the burr hole cover 1200 will be configured so that no component will extend further in towards the brain by a distance greater than the thickness of the cranial bone where the burr hole has been formed.

Referring now primarily to FIGS. 2A-2B and FIGS. 17 and 18, a method of using a burr hole cover according to some embodiments will be described. A lead 203 (or other medical instrument such as a catheter) may be partially implanted in the patient so that a distal portion of the lead 212 (or other medical instrument) extends distally from the burr hole towards and/or into the patient's brain (see, e.g., the direction represented by the arrow E in FIG. 3) and a proximal portion 210 of the lead (or other medical instrument) extends proximally from the burr hole away from the patient's brain (see, e.g., the direction represented by the arrow F in FIG. 3).

By the time the lead is implanted, the retainer 1210 may previously have been situated at the location of the burr hole so that the lead 203 is passing through the cap-receiving aperture 1214. If the retainer 1210 is provided with one or more bone-attaching apertures 1226 each configured to receive a bone-attaching elements such as bone screws, the retainer 1210 can be secured to the patient's cranium 202 using the bone screws. Depending on the configuration of the retainer 1210, it may be secured to the cranium 202 by other or additional means, such as an adhesive. When the user is placing the retainer 1210 in the burr hole, the user can situated the retainer 1210 so that any retaining elements or grooves 1232 are oriented in a particular direction relative to the patient's cranium and any other implanted or external device to which the implanted lead 203 is to be connected.

Depending on where the user wants the proximal portion 210 of the lead 203 to ultimately be located, the user can selected one of the grooves 1232 in which to situate the lead segment 206.

When the surgeon is ready to position the lead segment 206 in the retainer 1210, if the lead 203 has been provided with a stiffener such as a stylet which has not yet been removed, then the stiffener desirably is removed at this point. Then, once the user has selected a groove 1232 to use, the surgeon may press a proximal portion 210 of the lead at the burr hole, i.e., lead segment 206, down into one of the grooves 1232. If the retainer 1210 is provided with a channel 1258 associated with each groove 1232, then when the user situates the lead segment 206 in the groove, the portion of the lead extending distally of the lead segment 206 will be inclined to orient itself in the channel 1258. A rounded contour on the upper inner recessed area 1221 will discourage the lead from bending at a sharp 90 degree angle as the cap 1290 is pressed into the retainer 1210, and thus the lead segment 206 should traverse the channel 1258 and the associated groove 1232 more gently or gradually, avoiding any sharp bends in the lead 203.

When the lead segment 206 is positioned in one of the grooves 1232, and as was the case with the embodiments described with reference to FIGS. 1-11, a lead portion 210 extending proximally of the lead segment 206 can move relatively freely in a lateral direction (see the arrows G and H in FIG. 3) within the cut-out 1250 associated with the groove 1232. Because the lead segment 206 is captured within the burr hole cover 1200 at the groove 1232 and between the cap 1290 and the retainer 1210, the groove length 1231 can be relatively short and the groove depth 1233 (at least along the horizontal length 1231 of the groove) can be relatively deep, so as to keep the lead segment 206 that is constrained in the groove relatively small as compared to the overall length of the lead.

Desirably the channels 1258 and, similarly to the embodiments described with reference to FIGS. 1-11, each of the first and second groove ends 1252, 1254, the cut-outs 1250, are free of sharp edges or other obstacles that may stress portions of the lead that contact the burr hole cover 1200 before, during or after the burr hole cover 1200 is installed. Thus, these methods of installing the burr hole cover according to embodiments which allow relatively free lateral movement of the lead proximally and distally of a given groove are believed likely to minimize the stresses and strains on the portions of the lead that come in contact with the burr hole cover 1200 during or upon the installation process.

Once the lead segment 206 is situated in a groove 1232, the user may orient the cap 1290 so that the bottom of the cap is oriented over the cap-receiving aperture 1214 of the retainer 1210 and then press the cap 1290 into the retainer 1210. When the user does this, a portion of the cap 1290 will contact the lead segment 206, so that the lead segment is further secured between the groove and the cap.

Figure 9:
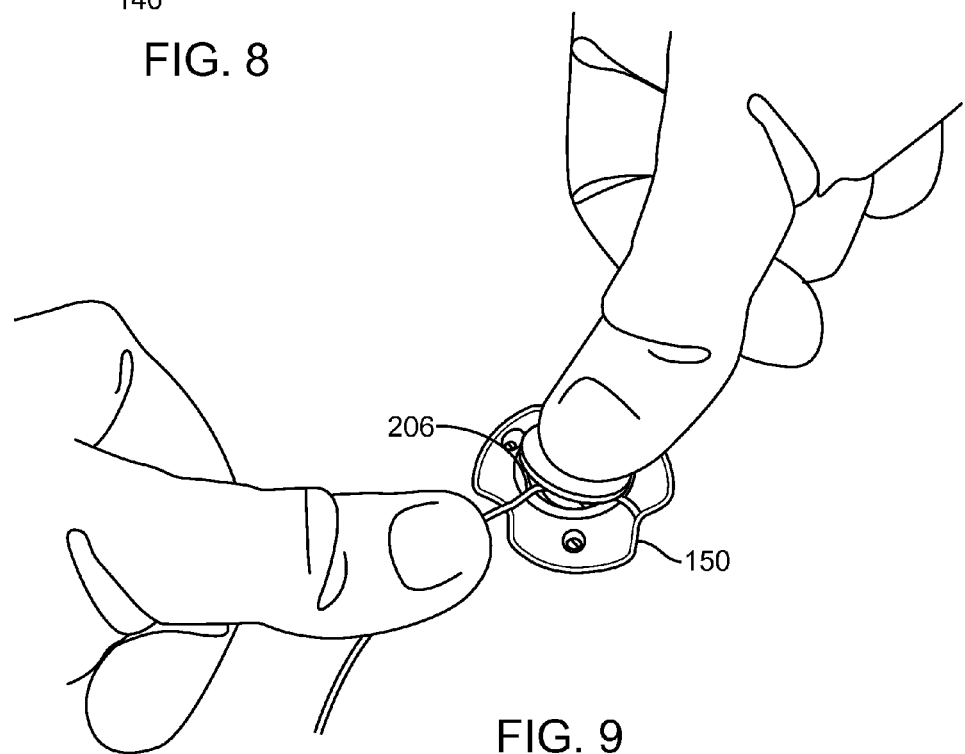
Figure 10:
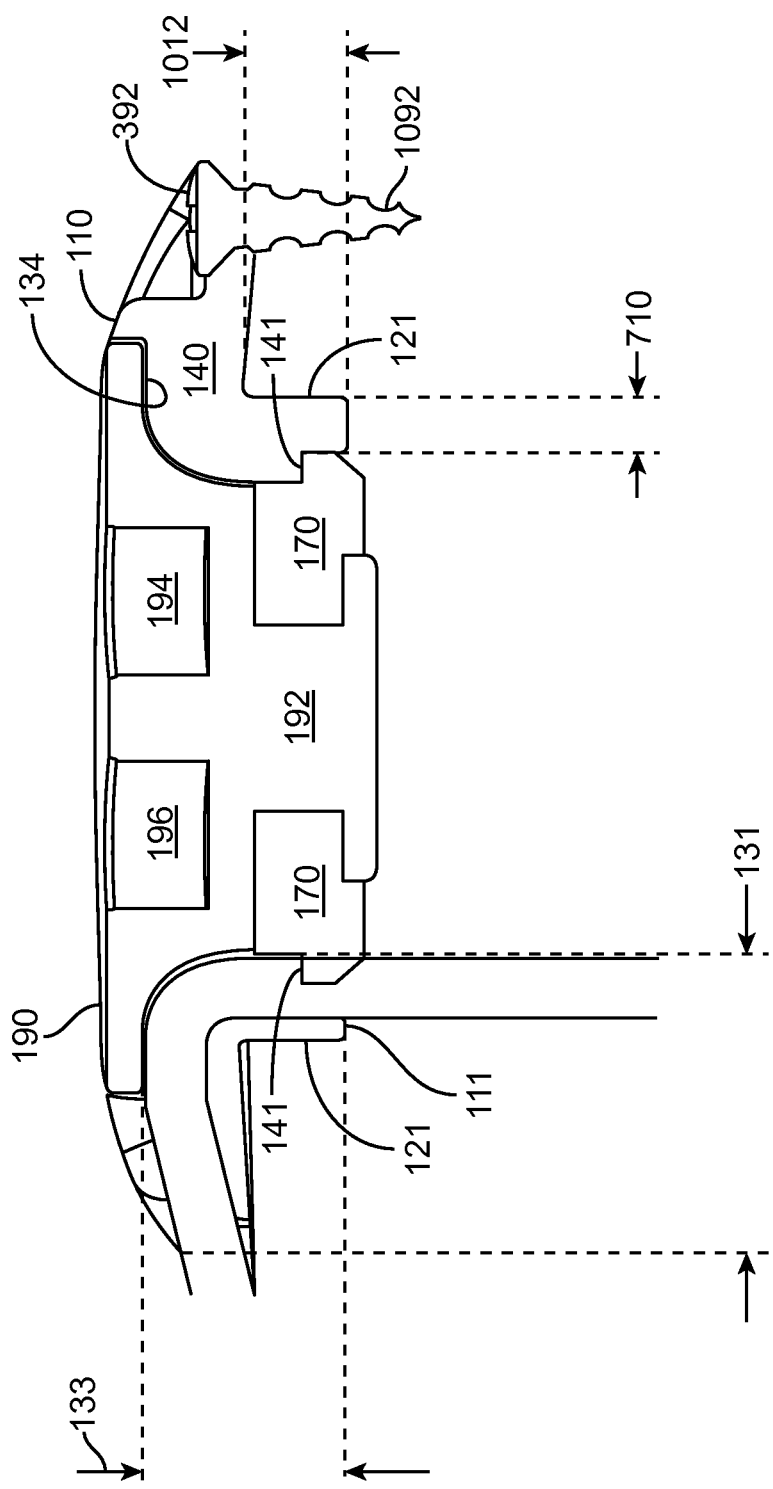
FIG. 10 is a cross-sectional view of a burr hole cover, according to an embodiment, installed to secure a portion of a medical device relative to the burr hole cover.
Figure 11:
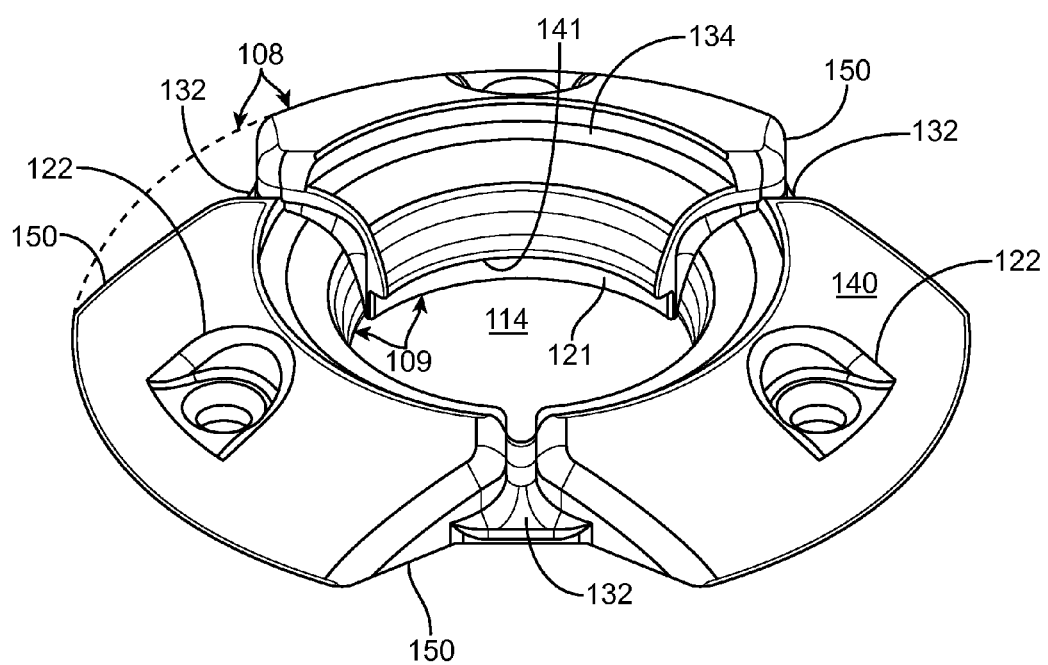
FIG. 11 is a perspective view of a retainer of a burr hole cover according to an embodiment.

Optionally, the user can further dress a portion of the lead extending proximally of the groove 1232 on the patient's skull as has been previously described with reference to FIGS. 8 and 9.

It will be appreciated that, as long as a retainer is provided with more than one retaining element 132 or 1232, a single burr hole cover may be used to secure more than one medical device, such as two lead segments 206.

Thus, embodiments provide for securing a lead to a burr hole, while avoiding sharp transitions and edges as the secured lead travels through the burr hole to the lead exit location. Further, the lead or medical device need only be restrained at one or two points along its length in order to fixate it in the burr hole cover, that is, in a retaining element (e.g., a groove) and where the cap presses the lead against the retainer. The smooth contours of the burr hole cover and the nature and number of attachment points for the medical device allow the medical device to be secured with minimal stress and little risk of compromising the integrity or function of the medical device.

Various example embodiments are thus described. All statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein but rather is defined by the appended claims.

The invention claimed is:

1. A burr hole cover for securing a medical device, said burr hole cover comprising
   a gasket having an outer diameter;
   a cap configured to receive the gasket;
   a retainer configured to receive the gasket and the cap and further configured to be partially positioned within a burr hole formed in a patient, the retainer comprising:
      a top defining an outer perimeter of the retainer and comprising an undersurface;
      a lower ring extending vertically downward from the undersurface and terminating at a predetermined depth, the lower ring comprising a bottom at the predetermined depth, wherein the bottom defines an inner perimeter of the retainer;
      a plurality of grooves provided in the top surface of the retainer, each of the plurality of grooves extending continuously from the inner perimeter, along the predetermined depth of the lower ring, and outward toward the outer perimeter of the top, and characterized by a groove depth, a groove width, and a groove length, and configured to receive a first segment of a medical device; and
      a plurality of cut-outs wherein each cut-out is provided at an end of a respective one of the plurality of grooves towards the outer perimeter and wherein each cut-out is configured to provide a range of at least lateral motion for a second segment of the medical device extending proximally out of the respective one of the plurality of grooves,
   wherein the outer diameter of the gasket is configured to retain the first segment of a medical device in a portion of one of the plurality of grooves, the portion being located at the inner perimeter of the retainer.

2. The burr hole cover of claim 1 wherein at least the groove depth corresponds to a diameter of the first segment of the medical device.

3. The burr hole cover of claim 1 wherein each of the plurality of grooves traverses a distance measured from a first end of the groove near the outer perimeter to the bottom of the lower ring.

4. The burr hole cover of claim 1 wherein the retainer further comprises a lower inner recessed area near the bottom of the lower ring and is configured to seat within a burr hole.

5. The burr hole cover of claim 1 wherein the retainer is provided with an upper inner recessed area for receiving at least one portion of the cap.

6. The burr hole cover of claim 1 wherein the retainer is provided with a varying height from the outer perimeter to the inner perimeter.

7. The burr hole cover of claim 1 wherein the gasket is formed from a first material and the retainer is formed from a second material and the first material is more resilient than the second material.

8. The burr hole cover of claim 1 wherein the gasket is formed from a first material and the cap is formed from a second material and the first material is more resilient than the second material.

9. The burr hole cover of claim 1, wherein the retainer is formed of a material having a durometer, the retainer comprising an undersurface and a material associated with the undersurface, the material associated with the undersurface having a durometer less than the durometer of the retainer.

10. The burr hole cover of claim 1, wherein the retainer is formed of a material having a durometer, the retainer comprising at least one insert associated with one of the plurality of grooves, the insert formed of a material having a durometer less than the durometer of the retainer.

11. The burr hole cover of claim 1, wherein at least one of the gasket and cap are formed of one of a clear material or an opaque material.

12. The burr hole cover of claim 1, wherein the cap comprises a top surface, and at least one of an aperture or recession formed in the top surface.

* * * * *